(12) United States Patent
Bjerken et al.

(10) Patent No.: US 9,320,509 B2
(45) Date of Patent: Apr. 26, 2016

(54) SUTURING DEVICES, SYSTEMS AND METHODS OF USING THE SAME

(75) Inventors: David Bernard Bjerken, Marietta, GA (US); Edward Lin, Decatur, GA (US)

(73) Assignee: Emory University, Atlanta, GA (US)

( * ) Notice: Subject to any disclaimer, the term of this patent is extended or adjusted under 35 U.S.C. 154(b) by 195 days.

(21) Appl. No.: 13/818,509

(22) PCT Filed: Aug. 24, 2011

(86) PCT No.: PCT/US2011/048932
§ 371 (c)(1),
(2), (4) Date: May 8, 2013

(87) PCT Pub. No.: WO2012/027449
PCT Pub. Date: Mar. 1, 2012

(65) Prior Publication Data
US 2013/0218174 A1    Aug. 22, 2013

Related U.S. Application Data

(60) Provisional application No. 61/376,336, filed on Aug. 24, 2010.

(51) Int. Cl.
```
A61B 17/04    (2006.01)
A61B 17/00    (2006.01)
A61B 17/30    (2006.01)
A61B 17/34    (2006.01)
A61F 5/00     (2006.01)
```

(52) U.S. Cl.
CPC ............ *A61B 17/04* (2013.01); *A61B 17/0469* (2013.01); *A61B 2017/00477* (2013.01); *A61B 2017/00818* (2013.01); *A61B 2017/047* (2013.01); *A61B 2017/0417* (2013.01); *A61B 2017/0472* (2013.01); *A61B 2017/306* (2013.01); *A61B 2017/3484* (2013.01); *A61F 5/0089* (2013.01)

(58) Field of Classification Search
CPC ............... A61B 17/04; A61B 17/0469; A61B 2017/00663; A61B 2017/306; A61B 2017/3484; A61B 2017/0472
USPC ......... 606/144, 145, 146, 139, 147, 148, 153; 227/179.1
See application file for complete search history.

(56) References Cited

U.S. PATENT DOCUMENTS

| | | | |
|---|---|---|---|
| 6,254,642 B1 * | 7/2001 | Taylor | A61F 2/0004 623/2.1 |
| 6,464,707 B1 * | 10/2002 | Bjerken | 606/139 |
| 2004/0082963 A1 | 4/2004 | Gannoe et al. | |
| 2004/0153167 A1 | 8/2004 | Stack et al. | |
| 2005/0075659 A1 * | 4/2005 | Realyvasquez | A61B 17/0682 606/167 |
| 2005/0149114 A1 * | 7/2005 | Cartledge | A61B 17/00234 606/213 |
| 2005/0177181 A1 | 8/2005 | Kagan et al. | |
| 2006/0253126 A1 * | 11/2006 | Bjerken et al. | 606/139 |
| 2006/0253142 A1 * | 11/2006 | Bjerken | A61B 17/00234 606/153 |
| 2007/0244493 A1 * | 10/2007 | Bjerken | A61B 17/0469 606/139 |
| 2009/0192531 A1 * | 7/2009 | Hsu | A61B 17/068 606/153 |
| 2010/0069930 A1 * | 3/2010 | Roslin | A61B 17/0057 606/151 |

* cited by examiner

*Primary Examiner* — Todd E Manahan
*Assistant Examiner* — Majid Jamialahmadi
(74) *Attorney, Agent, or Firm* — Emory Patent Group

(57) ABSTRACT

Provided herein are surgical suturing systems, devices, and methods of using the same. The systems and devices are optionally used in surgeries of the stomach.

26 Claims, 24 Drawing Sheets

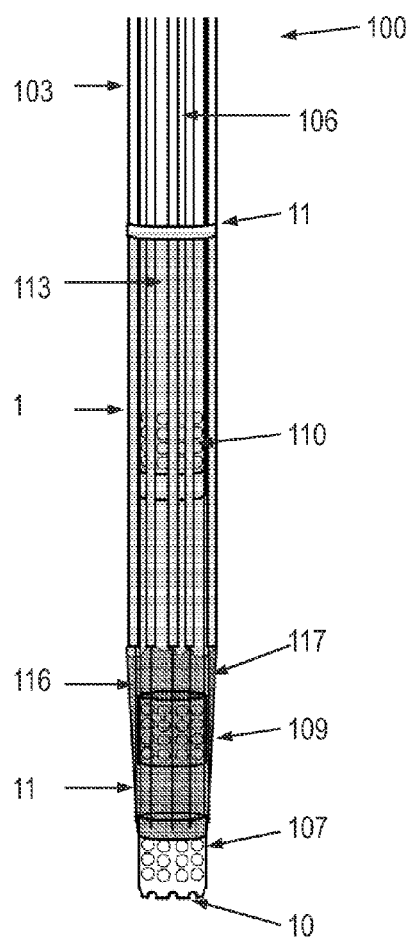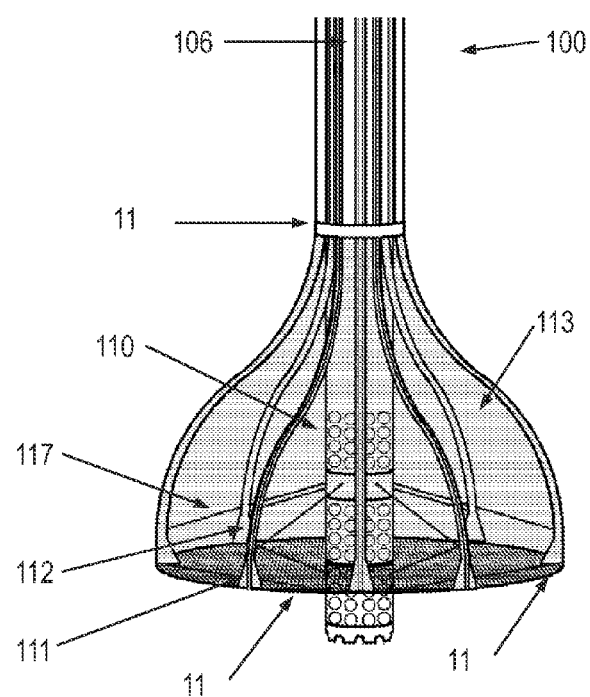
FIG. 2A
FIG. 2B

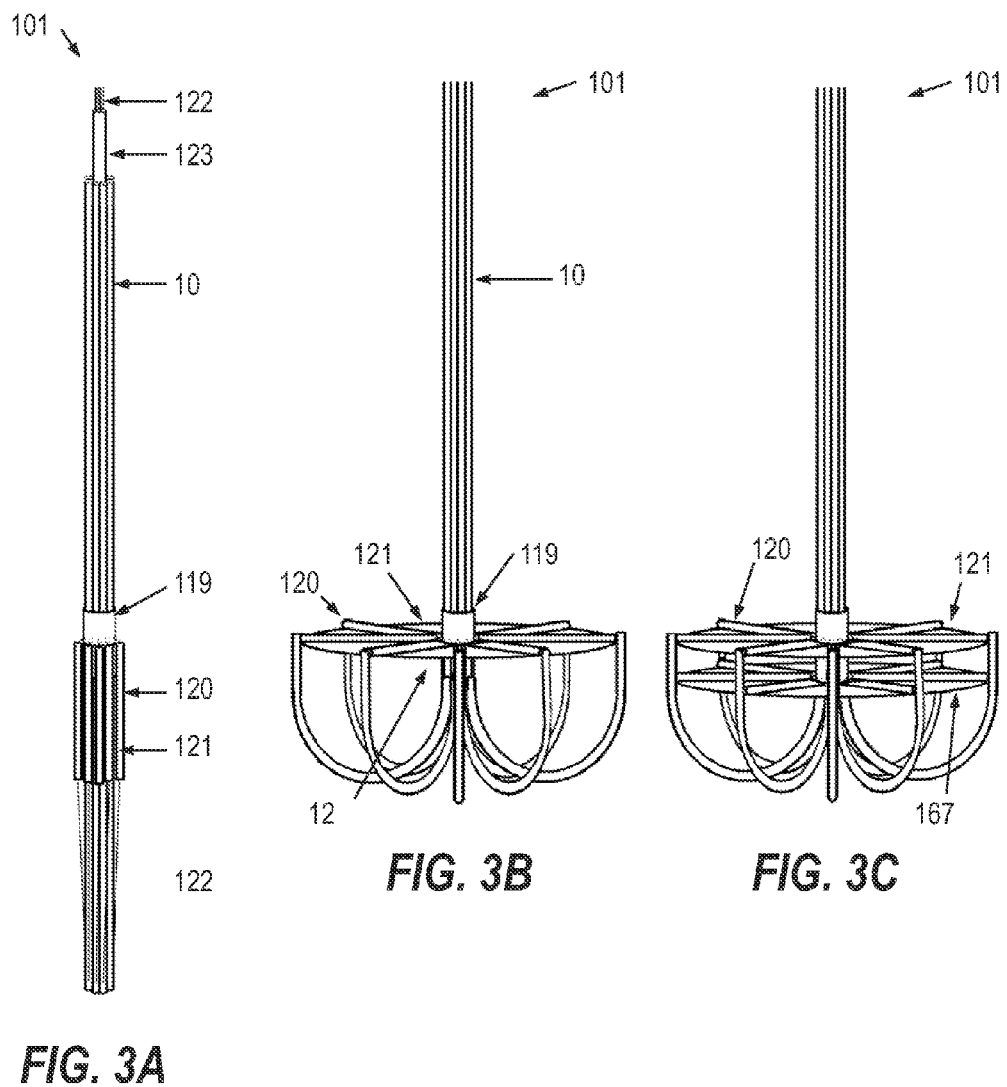

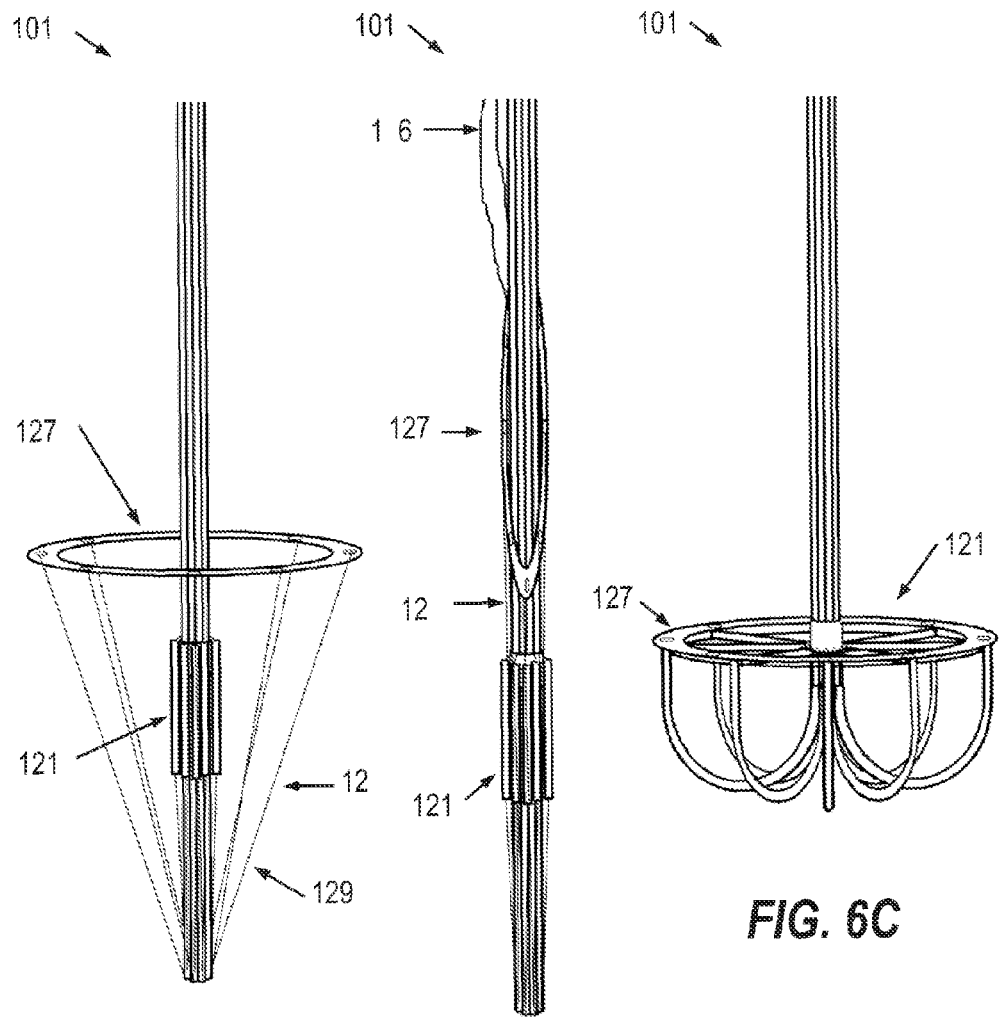

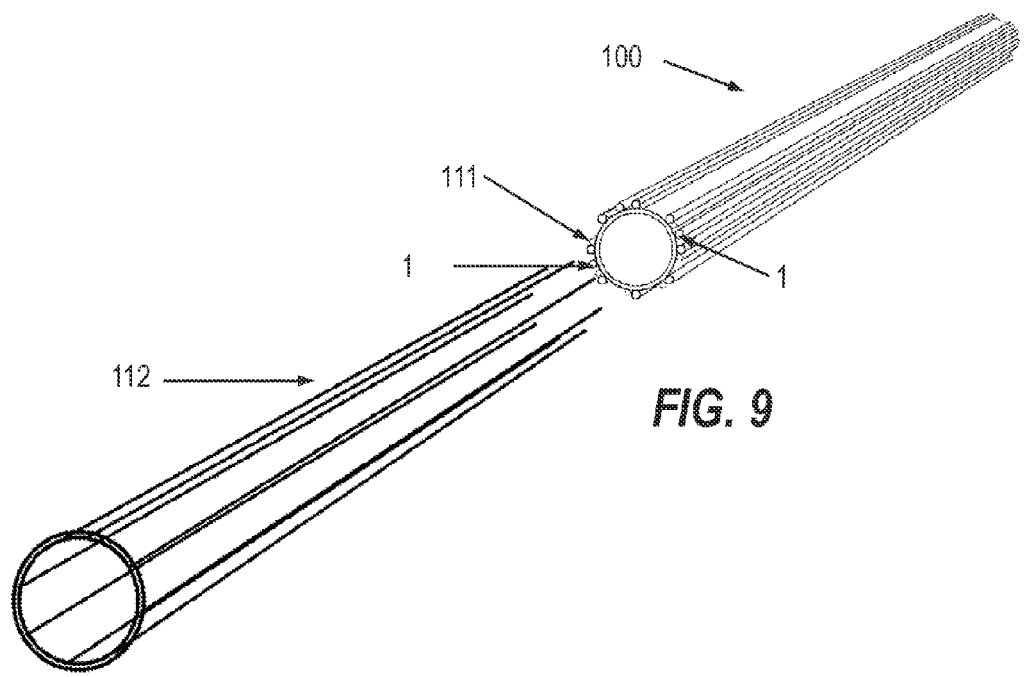
FIG. 9
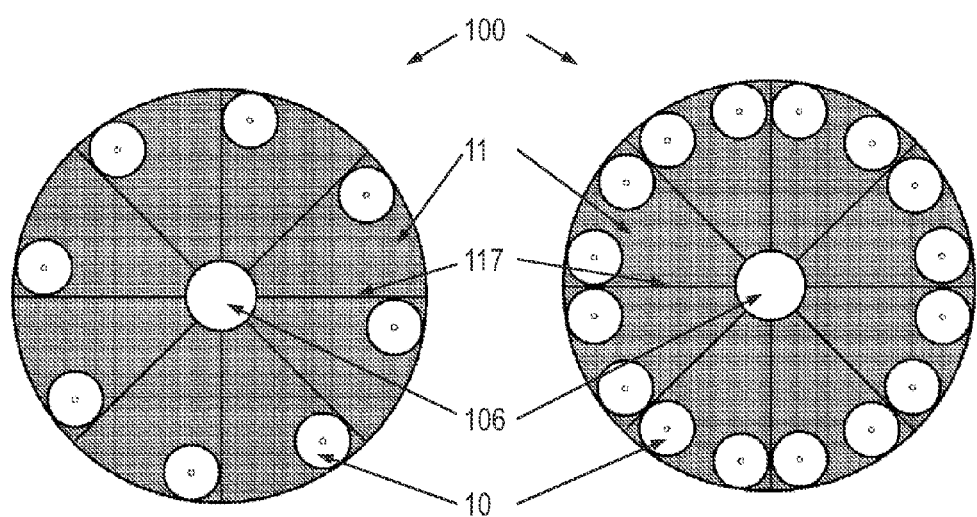
FIG. 10A  FIG. 10B

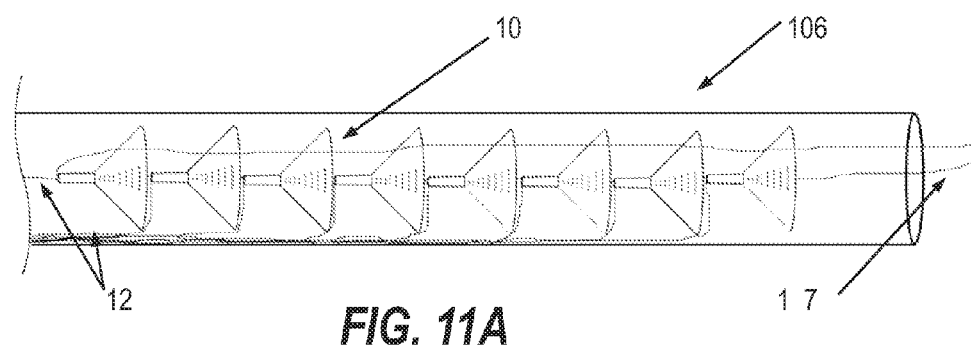
FIG. 11A
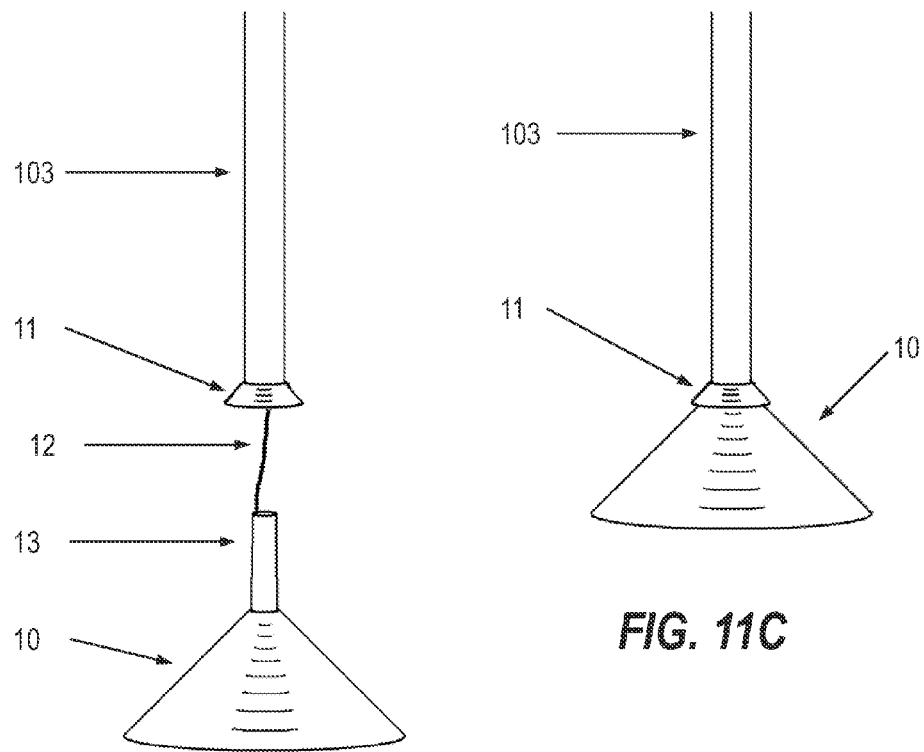
FIG. 11B
FIG. 11C

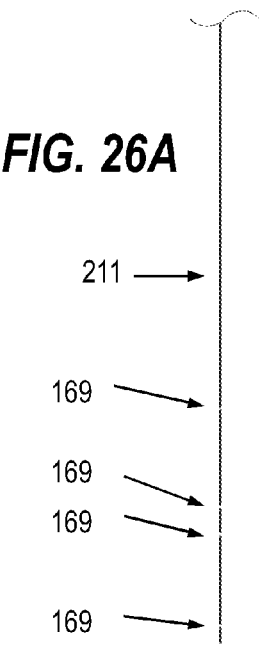
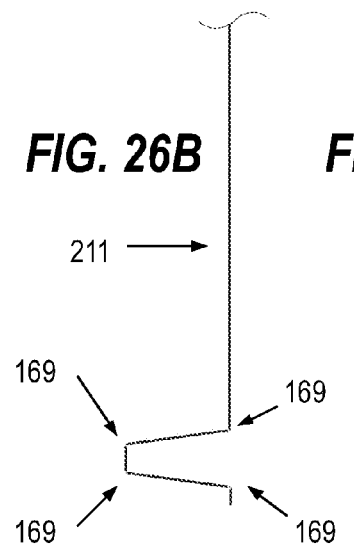
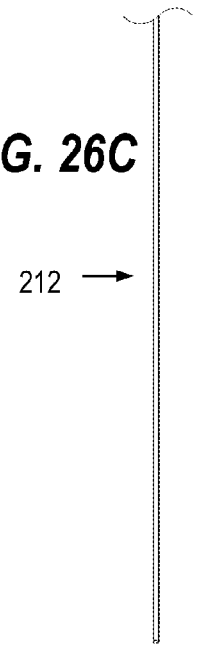
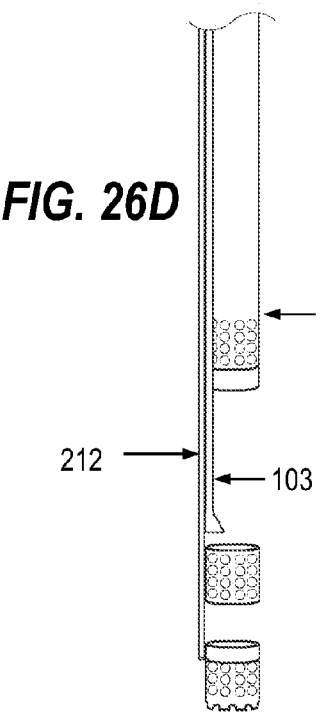
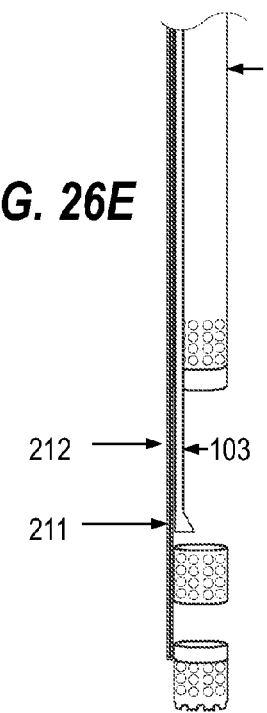
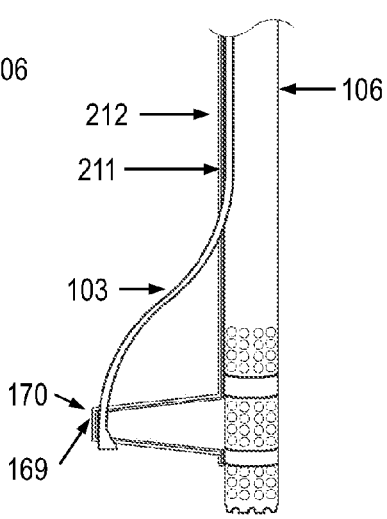

SUTURING DEVICES, SYSTEMS AND METHODS OF USING THE SAME

CROSS-REFERENCE TO RELATED APPLICATIONS

This application claims the benefit of U.S. Provisional Patent Application No. 61/376,336, filed Aug. 24, 2010, which is incorporated herein by reference in its entirety.

TECHNICAL FIELD

This document relates to surgical suturing systems and devices, and to methods of using the same.

BACKGROUND

Obesity is an overwhelming health problem. Among Americans age twenty and older, over 66 million are obese with nine million being morbidly obese. The US is by no means the only nation with a weight problem. The World Health Organization estimates there are some 1.7 billion overweight people in the world and 400 million obese people, creating what the WHO calls a "globesity epidemic." In 2006, over 200,000 bariatric surgeries were performed in the United States.

SUMMARY

Provided are systems, devices and methods for deploying sutures within a hollow organ.

An example system comprises a central tube having a lumen and an open distal end. An expandable enclosure is located about the central tube. The expandable enclosure is defined by a distal air-permeable surface and a lateral non air-permeable surface. The expandable enclosure further comprises a plurality of suture receiving tubes. Each suture receiving tube has an open distal end. The expandable enclosure is movable between a first retracted configuration and a second expanded configuration.

The example system further comprises an expandable suture delivery apparatus having a plurality of suture delivery tubes. Each suture delivery tube has an open distal end. The apparatus is configured for movement between a first retracted configuration and a second expanded configuration.

The suture delivery apparatus is slideably moveable thorough the central tube lumen while in its retracted configuration. The open distal end of one or more of the suture delivery tubes are distally spaced from and substantially alignable with one or more open distal end of a receiving tube while the suture delivery apparatus is in its expanded configuration.

Optionally, the open distal ends of the receiving tubes are spaced from each other and are arranged circumferentially about the enclosure when the enclosure is in its expanded configuration. Moreover, the open distal ends of the suture delivery tubes are optionally spaced from each other and are optionally arranged circumferentially about the suture delivery apparatus when the apparatus is in its expanded configuration.

The distal spacing between the distal ends of the delivery tubes and distal ends of the receiving tubes optionally define a circumferential gap between the apparatus and the expandable enclosure that is configured to receive tissue of the organ. Optionally, the open distal end of the central tube is located distal to the distal air-permeable surface when the enclosure is in its expanded configuration. Furthermore, the central tube optionally comprises at least one additional opening located within the enclosure. The additional opening is in fluid communication with the central tube lumen and the enclosure.

The central tube optionally comprises a suction port in communication with the lumen of the central tube. The suction port is adapted to be placed in communication with a suction source to evacuate air from the central tube lumen. The evacuation of air from the central tube lumen by the suction source causes organ tissue to enter the circumferential gap. The tissue drawn into the circumferential gap can be sutured during a surgical method, for example, as described herein. For example, the system optionally comprises a plurality of sutures that are passable from the distal end of each suture delivery tube, through the organ tissue entered into the circumferential gap, and into the aligned distal ends of the receiving tubes. Optionally, one or more suture comprises an elongated flexible needle.

Optionally, the example system comprises between two and twelve receiving tubes. Optionally, the example system comprises eight receiving tubes. Optionally, the example system comprises between two and twelve suture delivery tubes. Optionally, the example system comprises eight receiving tubes. Optionally, the number of receiving tubes is equal to the number of suture delivery tubes.

The example system can optionally further comprise an actuator mechanism configured for moving the enclosure between its retracted and expanded configuration and an actuator mechanism configured for moving the suture delivery apparatus between its retracted and expanded configuration. The one or more actuator mechanisms are optionally configured for remote operation by an operator located outside of the organ lumen.

The example system can optionally further comprise a distal ring graft positionable proximal to the open distal ends of the suture delivery tubes and distal to the open distal ends of the suture receiving tubes. Optionally, the distal ring graft is moveable through the central tube lumen. Optionally, a plurality of sutures is passable from the distal end of each suture delivery tube, through the organ tissue entered into the circumferential gap, and into the aligned distal ends of the receiving tubes.

The example system can optionally further comprise a proximal ring graft positionable proximal to the distal ring graft. Optionally, the diameter of the proximal ring graft is smaller than the diameter of the distal ring graft. Optionally, the diameter of the proximal ring graft is larger than the diameter of the distal ring graft. Optionally, the diameter of the proximal ring graft is substantially the same as than the diameter of the distal ring graft.

The open distal end of the central tube is optionally positionable in the lumen of a hollow organ. Moreover, at least a portion of the enclosure is optionally positionable in the lumen of the hollow organ.

The suture delivery apparatus of the example system is also optionally positionable in the lumen of the hollow organ. The enclosure and suture delivery apparatus are optionally moveable between their expanded and retracted configurations within the organ lumen and the enclosure and suture delivery apparatus are optionally introduced into the organ lumen and/or removed from the organ lumen in their retracted configurations.

In some examples, a portion of the central tube is located outside of the organ lumen when the open distal end of the central tube is positioned in the lumen of the hollow organ. Moreover, a portion of the suture receiving tubes and a portion of the suture delivery tubes are optionally located outside of the organ lumen when the enclosure and the delivery apparatus are positioned within the organ lumen. Optionally, the organ is a stomach. Optionally, the distal open end of the central tube and the enclosure are configured to be orally passed into a subject, and to be advanced through the esophagus of the subject and into the stomach of the subject.

The central tube has an outer surface and a longitudinal axis. Optionally, at least one suture receiving tube is distanced from the longitudinal axis at plane perpendicular to the longitudinal axis by about 3.0-6.0 centimeters or more when the enclosure is in its expanded configuration. For example, at least one suture receiving tube may be distanced from the longitudinal axis at plane perpendicular to the longitudinal axis by about 4.0 centimeters when the enclosure is in its expanded configuration In some example systems, the distal open end of the suture receiving tubes are expandable to an increased diameter. Optionally, the example system includes one or more funnel devices with a larger distal diameter relative to a narrowed proximal diameter. The funnel devices are positionable within one or more suture receiving tubes.

An example system for deploying sutures within a hollow organ comprises a central tube having an outer surface and a lumen with an open distal end. The system further comprises a proximal enclosure having a plurality of suture receiving tubes. Each suture receiving tube has an open distal end. The enclosure is moveable between a retracted configuration and an expanded configuration. The system further comprises a distal suture delivery apparatus having a plurality of suture delivery tubes. Each suture delivery tube has an open distal end. The delivery apparatus is moveable between a retracted configuration and an expanded configuration. The expanded enclosure is spaced from the expanded delivery apparatus to define a circumferential gap therebetween the enclosure and the delivery apparatus. The central limit of the gap is defined by a portion of the central tube outer surface.

Optionally, the suture delivery apparatus is slideably moveable thorough the central tube lumen while in its retracted configuration and wherein the open distal end of one or more of the suture delivery tubes are distally spaced from and substantially alignable with a corresponding open distal end of a receiving tube when the suture delivery apparatus is in its expanded configuration. Optionally, the proximal enclosure is located about the central tube. Optionally, the enclosure comprises a distal surface that is permeable to air and a lateral surface that is impermeable to air. The distal opening of the central tube is optionally located distal to the permeable surface. While the distal opening of the tube is located distal to the permeable surface, the central tube optionally defines a passage for communication of air between the enclosure and the central tube lumen. Negative pressure applied to the central tube lumen draws air through the permeable surface, into the enclosure, through the passage and into the central lumen. The negative pressure can draw tissue towards the central tube. For example, the enclosure and the suture delivery apparatus are optionally positioned within the hollow organ and the application of the negative pressure draws organ tissue into the circumferential gap.

The example system optionally further comprises one or more sutures configured to be passed from at least one suture delivery tube, though the tissue in the circumferential gap, and into a corresponding suture receiving tube.

Also provided is an example system for deploying sutures within a hollow organ including a central tube having an outer surface and a lumen with an open distal end. The example system comprises a proximal enclosure having a plurality of suture receiving tubes. Each suture receiving tube has an open distal end, wherein the enclosure is moveable between a retraced configuration and an expanded configuration. The system further comprises a distal suture delivery apparatus having a plurality of suture delivery tubes. Each suture delivery tube has an open distal end. The delivery apparatus is moveable between a retracted configuration and an expanded configuration. The suture delivery apparatus is slideably moveable thorough the central tube lumen while in its retracted configuration.

Optionally, the open distal end of one or more of the suture delivery tubes are distally spaced from and substantially alignable with a corresponding open distal end of a receiving tube when the suture delivery apparatus is in its expanded configuration. For example, the expanded enclosure is optionally spaced from the expanded delivery apparatus to define a circumferential gap therebetween the enclosure and the delivery apparatus, with the central limit of the gap being defined by a portion of the central tube outer surface. Optionally, the proximal enclosure is located about the central tube and includes a distal surface that is permeable to air and a lateral surface that is impermeable to air. The distal opening of the central tube is optionally located distal to the permeable surface. The central tube optionally defines a passage for communication of air between the enclosure and the central tube lumen. Negative pressure applied to the central tube lumen draws air through the permeable surface, into the enclosure, through the passage and into the central lumen. Optionally, the enclosure and the suture delivery apparatus are positioned within the hollow organ and the application of the negative pressure draws organ tissue into the circumferential gap. The system may optionally comprise one or more sutures configured to be passed from at least one suture delivery tube, though the tissue in the circumferential gap, and into a corresponding suture receiving tube.

Also provided are methods for deploying sutures within a hollow organ. For example, a method for deploying sutures within a hollow organ, comprising directing a suture receiving apparatus into the hollow organ. The suture receiving apparatus comprises a central tube having lumen, an open distal end and a plurality of suture receiving tubes. The suture receiving apparatus further comprises an enclosure that is moveable between a first retracted configuration and a second expanded configuration. The suture receiving apparatus is directed into the hollow organ in its retracted configuration.

The example method further comprises directing a suture delivery apparatus into the hollow organ. The suture delivery apparatus comprises a plurality of suture delivery tubes and is moveable between a first retracted configuration and a second extended configuration. The suture delivery apparatus is directed into the hollow organ by passage through the central tube lumen and distal open end while in its retracted position. The suture delivery apparatus is expanded in the organ such that the open distal end of one or more of the suture delivery tubes are distally spaced from and substantially aligned with a corresponding open distal end of a receiving tube when the suture delivery apparatus is in its expanded configuration. One or more sutures are passed from at least one suture delivery tube into at least one aligned suture receiving tube. Tissue of the hollow organ can then be sucked between one or more of the aligned suture delivery tubes and suture receiving tubes and one or more suture can be passed through the tissue of the hollow organ between the suture tube and the suture receiving tube as the suture passes from the suture delivery tube into the receiving tube. The suture delivery apparatus and suture receiving apparatus can be moved to their retracted configurations for removal from the organ.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 2A is a schematic diagram illustrating a view of an unexpanded outer tube component.

FIG. 2B is a schematic diagram illustrating a view of an expanded outer tube component.

FIG. 3A is a schematic diagram illustrating a cut a way view of an un-expanded suture delivery tube set component.

FIG. 3B is a schematic diagram illustrating a view of an expanded suture delivery tube set component.

FIG. 3C is a schematic diagram illustrating a view of an expanded suture delivery tube set component with two platforms.

FIG. 6A is a schematic diagram illustrating a view of a delivery tube set component incorporated with a ring graft.

FIG. 6B is a schematic diagram illustrating a view of a delivery tube set component incorporated with a ring graft positioned for insertion.

FIG. 6C is a schematic diagram illustrating a view of a delivery tube set component incorporated with a ring graft positioned for deployment.

FIG. 9 is a schematic diagram illustrating a view of a segment view of an outer tube and a stiffening wire set.

FIG. 10A is a schematic diagram illustrating a bottom view of an expanded outer tube with eight receiving tubes.

FIG. 10B is a schematic diagram illustrating a bottom view of an expanded outer tube with sixteen receiving tubes.

FIG. 11A is a schematic diagram illustrating a view of a series of funnels contained in a tube.

FIG. 11B is a schematic diagram illustrating a view of a receiving tube with a partially incorporated funnel.

FIG. 11C is a schematic diagram illustrating a view of a receiving tube with an incorporated funnel.

FIG. 26A is a schematic diagram illustrating a support multi-segmented support rod in a linear configuration.

FIG. 26B is a schematic diagram illustrating a multi-segmented support rod in a non-linear configuration.

FIG. 26C is a schematic diagram illustrating a support rod tube configured to accept the multi-segmented support rod of FIGS. 26A and 26B.

FIG. 26D is a schematic diagram illustrating the support rod tube attached in proximity to a distal portion of the central tube of an example suturing device.

FIG. 26E is a schematic diagram illustrating the support rod tube attached in proximity to a distal portion of the central tube of an example suturing device wherein a multi-segmented support rod is positioned therein the support rod tube in its linear configuration.

FIG. 26F is a schematic diagram illustrating the support rod tube attached in proximity to a distal portion of the central tube of an example suturing device wherein a multi-segmented support rod is positioned therein the support rod tube and the support rod tube and multi-segmented support rod are in non-linear configurations.

Like reference symbols in the various drawings indicate like elements.

DETAILED DESCRIPTION

Figure 1:
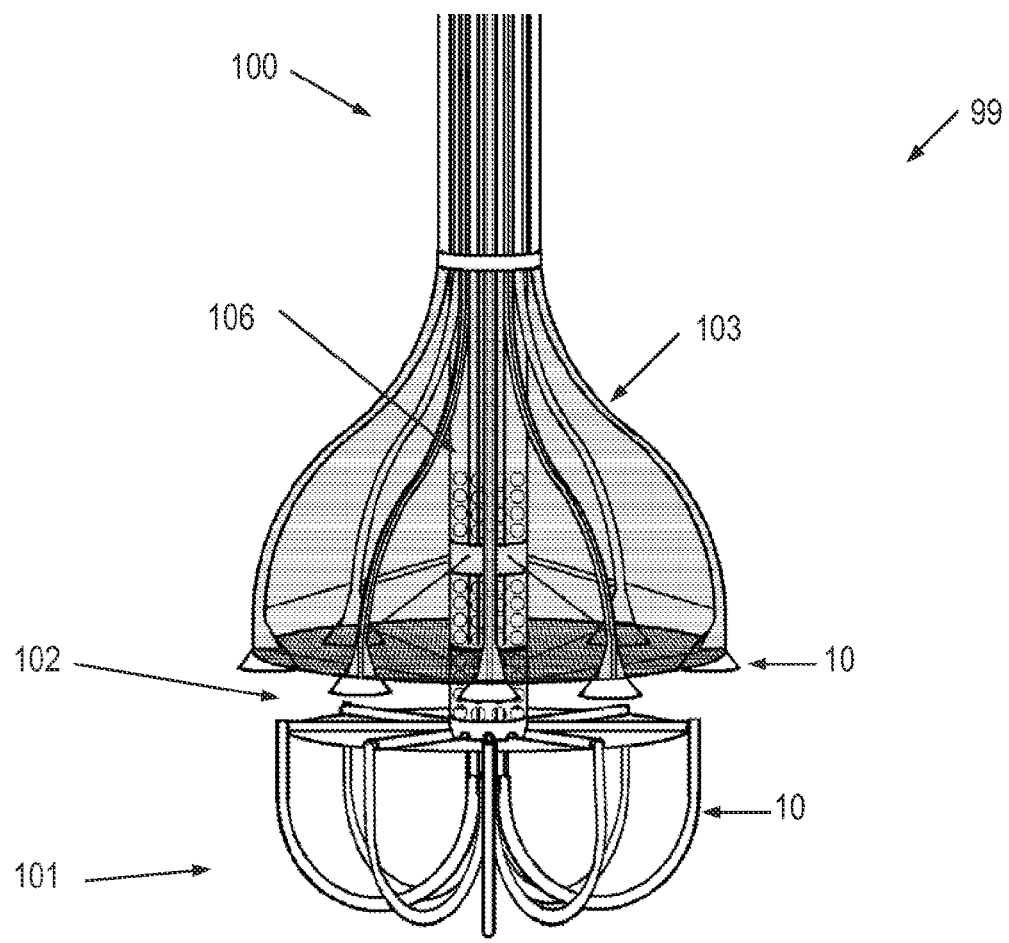
FIG. 1 is a schematic diagram illustrating a view of an example suturing system including expanded outer tube component incorporated with an expanded delivery tube set component.

Methods that have been used to treat obesity include gastric bypass and small bowel bypass surgery. Stapling of portions of the stomach has also been used to treat morbid obesity, which includes both vertical and horizontal stapling and other variations that are intended to reduce the size of the stomach and make a small stoma opening.

Many problems have been associated with the use of staples. First, staples are undependable. Second, they may cause perforations in the stomach wall. And third, the pouch or the stoma formed by the staples may become enlarged over time, making the procedure useless.

Another method for weight control employs the placement of a band around a portion of the stomach by open or laparoscopic surgery thereby compressing the stomach and creating a stoma that is less than the normal interior diameter of the stomach. The constricted stoma restricts food intake into the lower digestive portion of the stomach.

These devices, known as gastric bands, require a surgical procedure for their implantation, which includes accessing the patient's stomach and other internal organs via incisions. The morbidity related to these surgical procedures can cause pain, prolonged recovery, complications, and expense to the patient and to the healthcare system. The procedure can also be technically challenging for the surgeon.

Performing surgical procedures through a patient's natural orifice is highly desirable and has many benefits over using more invasive open surgical and laparoscopic methods.

The present application describes endoscopic circumferential suturing devices and systems that provide advantages for performing endoluminal procedures, including operative enhancements for reliable and straightforward access to the stomach, technical innovations that enable complex and aggressive augmentation of tissues, and resulting clinical improvements enabled by large circumferential serosal-to-serosal tissue augmentation, which has been shown to produce long-term durability and efficacy.

The devices and systems described herein optionally relate to endolumenal surgical procedures for the treatment and control of obesity and, more particularly, to devices and method for the endoscopic implantation of suture and incorporated prosthetic grafts.

The described devices and systems can be used in methods for suturing tissue and implanting grafts within a hollow organ or closed body cavity such as the stomach. As used herein, "hollow organ" may refer to any hollow organ or body cavity.

The systems, devices and methods optionally utilize long flexible needles attached to sutures, which are passed through a plurality of long flexible tubes which are contained as parts of a two component system.

The outer tube component of the device is designed to be inserted into the patient's stomach first. Once the distal end of the outer tube component is in the stomach, the distal end of the component is expanded circumferentially. In this regard the distal end of the component can comprise an expandable enclosure. Therefore, for example, when the outer tube component is referred to as having being expandable or expanded the expandable enclosure about the central tube of the outer tube component is moving between a retracted and expanded configuration. Thus, the outer tube component 100 optionally comprises a central tube and an expandable enclosure.

The expandable enclosure of the outer tube component can further comprise suture receiving tubes, also referred to herein as receiving tubes, positioned around the circumference of the expandable enclosure, which when the distal end of the outer tube component, for example the expandable enclosure, is expanded, radiate outward from the central lumen of the outer tube component.

Subsequent device components may be passed through the central lumen of the outer tube component. Optionally, a plurality of funnel tips are pulled through the central lumen of the central tube and then into the distal ends of the plurality of receiving tubes and secured in place, thereby increasing the diameter size of the receiving tube's distal ends.

An expandable suture delivery apparatus also referred to as a suture delivery tube set component is then passed through the central lumen of the outer tube component until the distal end emerges through the distal end of the outer tube component. The distal end of the suture delivery tube set can be manipulated remotely by the operator such that the tips of the distal ends of a plurality of suture delivery tubes, also referred to herein as delivery tubes each bend outward approximately 180 degrees and spread circumferentially to align with and directly oppose the corresponding receiving tubes of the outer tube component. By having the delivery tubes bent to an approximate 180 degrees as opposed to a configuration greater than 180 degrees, there is less resistance for the passage of long flexible needles through the bend.

The space created between the bottom of the expanded outer tube component and the top of the expanded section of the suture delivery tube set component is a circumferential gap, across which a plurality of suture needles can be passed. This gap allows tissue to be drawn into the space between the two components when suction is applied to the outer tube component which is in fluid communication with a vacuum source. The gap can allow 2.0 cm or more tissue to be drawn radially into the gap, which can form a circumferential invagination or plication of tissue to be sutured. A tissue placation of this depth creates an apposition of the serosal, or non-lumenal side, of the stomach tissue, forming a serosal to serosal tissue placation. For example, the serosal-to-serosal tissue invaginated into the gap, creating a plication, can be drawn in circumferentially around the gap. Optionally, tissue is drawn in such that the distance from the medial extent of tissue invagination, or plication, to one or more suture delivery tube opening or one or more suture receiving opening is about 3.0 cm or more.

The circumferential gap of the device allows a circumferential acquisition of tissue of the stomach or cavity in which it is operating. Because the device is able to expand to a diameter closely matching the diameter of the region of the organ to be engaged, it is able to invaginate the entire perimeter of the organ.

With tissue drawn into the gap, long flexible wire needles connected to sutures are pushed through the delivery tubes, across the gap, traversing acquired tissue, into the receiving tubes, and through the receiving tubes. The distal end of the sutures may be attached directly to a graft, such as a ring, or they may be attached to a suture anchor, such as a T-tag.

Optionally, the result of a method of deploying sutures within a hollow organ, when the organ is a stomach, is a gastric constriction in a portion of the stomach, for example an upper portion of the stomach. This constriction may be created by attaching a first, or distal ring to a second or proximal ring, with a circumference of tissue held between the two rings. The incorporation of the distal ring with a circumference of tissue is accomplished by 1) utilizing a ring directly incorporated with a plurality of sutures around the body of the ring's circumference, or 2) utilizing a ring which is penetrated with a plurality of sutures around the body of its circumference and which the sutures incorporate a suture anchor, such that the sutures pass through the body of the ring until the point where the suture anchor makes contact with the ring body.

The distal ring is loaded into the suture delivery tube set component by 1) having the directly incorporated sutures inserted into the delivery tubes, thereby being releasably held to the suture delivery tube set component, or by 2) having a set or directly incorporated retaining threads inserted into a) the delivery tubes, or b) the dedicated retaining tubes or channels of the suture delivery tube set component, thereby being releasably held to the suture delivery tube set component. When the distal end of the suture delivery tube set is reconfigured from its linear configuration to its expanded circumferential configuration the ring is; 1) held in position over the distal ends of the delivery tubes, or 2) held in position within the circumference of the of the expanded circumference of the distal ends of the delivery tubes, or 3) in held in a ring holder distal to the expanded circumference of the distal ends of the delivery tubes.

The long flexible needles are positioned in the suture delivery tube set such that the sharpened distal ends of the needles are contained within the distal end of the delivery tubes. The needles are of such a length that they are at least as long as the collective distance of delivery tube, the suction opening, and the receiving tube. When the distal ends of the delivery tubes are warped, the flexible needles contained within are warped as well.

With the tip of the needle being positioned distal to the radius of the bend in the delivery tube, the flexible needle pushes through the tube with ease. Conversely, if the needle tips were positioned proximal to the radius of the bend, the needle tip would meet more resistance, making it harder to push the needle through the bend and potentially having the needle tip penetrate the bore of the delivery tube at the point of resistance.

The component nature of the described systems and devices allows the needles to enter the surgical site in a relatively straight configuration, and then be remotely reconfigured to a position suitable for effectively traversing tissue and traveling back out of the device and patient. The long flexible needles are pushed by the operator through the delivery tubes, across the circumferential opening and into the receiving tubes until they emerge from the proximal end of the receiving tubes, at which point the operator grasps the distal end of the needles and pulls the needles and attached sutures completely to their point of graft or anchor incorporation with tissue.

Subsequent to needle and suture deployment, the device may begin to be systematically disassembled enabling the components to be withdrawn from the patient. The distal end of the suture delivery tube set component is manipulated remotely by the operator and reconfigured to a substantailly linear (e.g. retracted) configuration. The suture delivery tube set component is subsequently pulled out of the central lumen of the outer tube and out of the patient.

Subsequent to suture delivery tube set component withdrawal, the expanded distal end of the outer tube component is un-expanded (e.g. retracted), remotely by the operator and reconfigured into its relatively straight tubular configuration. The outer tube component is subsequently withdrawn from the stomach and out of the patient. The distal end of the sutures and incorporated ring are anchored by the currently incorporated tissue enabling the lengths of sutures to "flow" out of the distal end of the receiving tubes as the outer tube component is withdrawn from the patient. Suture order may be maintained once the sutures are completely withdrawn from the receiving tubes by the use of a circular suture organizer or other suture organization systems.

The funnels and their attached strings optionally remain in place as the outer tube component is withdrawn, with each funnel encircling a deployed suture. The funnel strings are then pulled by the operator up and out of the patient.

The plurality of sutures may be incorporated with a second graft, such as a ring graft by passing the sutures through the body of the second ring graft. The second graft may be slid down the plurality of sutures using a graft pusher. This is known by those skilled in the art as parachuting the graft into place.

The second ring graft is optionally pushed into position proximal to the acquired tissue and the distal ring graft, and using tension of the sutures to pull the distal ring upward while using downward pressure with the ring pusher, or other endoscopic device such as an endoscope, to push the second ring downward, the two rings couple together with a snap fit. Optionally, the first ring may be secured to the second by utilizing a t-tag attachment, or, optionally, suture crimping devices may be utilized, or, optionally, by tying one suture arm to an adjacent suture arm. Subsequent to graft to graft fixation, the extra lengths of suture material may be cut using endoscopic instrumentation.

The resulting deployment of circumferential sutures and the subsequent ring graft to ring graft fixation with incorporated circumferential tissue therein, is a constriction in the stomach that may impede the flow of ingested food and thereby may lead to reduced solid food consumption by the patient, thereby enabling the patient to lose excess body weight.

FIG. 1 illustrates an example endoscopic circumferential suturing device. The device 99 includes an outer tube component 100 comprised of a central tube 106 surrounded by a plurality of smaller receiving tubes 103. The suture delivery tube set 101 has the ability to pass its distal end through the central tube 106 of the outer tube component 100. The distal end of the suture delivery tube set 101 has been remotely reconfigured in this illustration, demonstrating how the distal end of the delivery tubes 104 are directed toward the receiving tubes 103 of the outer tube 100. The reconfigured distal end of the suture delivery tube set component is maintained a distance from the expanded outer tube component creating a circumferential gap 102 into which tissue may be drawn.

As illustrated in FIG. 2A, the outer tube component 100 has a substantially linear tube shape in its un-expanded, retracted configuration. This retracted configuration facilitates insertion into a patient's digestive tract. The flexible nature of the outer tube component further facilitates insertion into a patient's digestive tract. The outer tube component 100 may subsequently have stiffening wires 112 inserted into dedicated expansion rib tubes 111 spaced around the circumference of the outer tube component 100. These expansion rib tubes 111 and their contained stiffening wires 112 provide the vertical support for the expandable section of the outer tube component, the expandable enclosure, when expanded.

The expansion rib tubes 111 are positioned adjacent to the receiving tubes 103 which encircle the central tube 106 of the outer tube and together have the ability to radiate outwardly distal to the containing ring 115. The figures illustrate a device having eight receiving tubes 103 and eight delivery tubes 104, but more receiving tubes and delivery tubes as well as fewer receiving and delivery tubes are possible. The containing ring 115 maintains the position of expansion rib tubes 111 and receiving tubes 103 and provides the proximal endpoint to their radial expansion.

The containing ring 115 is also the proximal attachment point for the flexible impermeable material 113 which makes up the outer covering of the expandable enclosure, also referred to herein as the expandable section, of the outer tube component 100.

The expandable section of the outer tube is able to expand in a fashion similar to an umbrella. The distal holey tube segment 107, which may be made of a rigid material such as steel, titanium, or plastic, is attached to flexible actuating wires 116 which may be actuated up and down by an operator through dedicated actuator wire containing tubes 155 contained around the central tube 106.

Optionally, the distal holey tube segment 107 is attached to two actuating wires 116 positioned on opposing sides of the distal holey tube segment's 107 circumference. When the distal holey tube segment 107 is actuated upward, the attached umbrella struts 117 are forced outward, thereby forcing the attached expansion rib tubes 111 and their contained stiffening wires 112, as well as the adjacent receiving tubes 103 outward. The two ends of the upper umbrella struts 117 are attached at one end, to points on the distal end of the central tube 110, and at the other end, to points on the distal end of the expansion rib tubes 111. The two ends of the lower umbrella struts 117 are attached, at one end, to the proximal end of the distal holey tube segment 107, and at the other end, to points on the distal end of the expansion rib tubes 111.

The upper umbrella struts have the same length as the lower umbrella struts. The point of connection of the upper umbrella strut 117 to the expansion rib tube 111 is separated by a distance to the point of connection of the lower umbrella strut 117 to the expansion rib tube 111, thereby enabling the portion of the expansion rib tube between the two umbrella strut connections to remain relatively parallel to the central tube 106 when the expandable section of the outer tube 100 is expanded.

The actuating wires 116 may pass freely through channels in the middle holey tube section 109 so that it "floats" on the wires 116 between the distal holey tube section 107 and the distal end of the main central tube 110. The middle holey tube segment 109 is made of a rigid material and is able to be actuated upward by being pushed upward by the distal holey tube segment 107 until it contacts the distal end 110 of the main central tube.

The middle holey tube segment 109 may not actuate downward past a specific point as it is attached to a restraining wire that limits the distance of its decent as it floats on the actuating wires 116. The restraining wire may be similar to the actuating wire 116 and contained in a tube similar to the actuating wire containing tube 155 but the free moving wire cannot descend past a point as the proximal end of the wire is capped or bent, thereby preventing further decent in the containing tube.

The separate segments of rigid holey tubes 107, 109, 110 enable the distal end of the outer tube to remain relatively flexible and only have short segments of rigidity spaced over a longer distance when in the un-expanded configuration, thereby facilitating insertion into a natural orifice of a patient. When the segments of rigid holey tubes are actuated and pulled together, they combine to create a longer rigid section of the central tube 106 which enhances stability to the expanded distal end of the outer tube 100. The holes or perforations in the rigid holey tube segments 107, 109, 110 allow suction to communicate through the holes and into the expanded suction enclosure of the outer tube component 100 when a vacuum is applied to the central tube 106. Optionally, the separate segments of rigid holey tubes may be approximately 1.0 to 4.0 centimeters in length.

Optionally, as shown in FIGS. 26A-26F, the struts comprise multi-segmented rods 211 positioned within rod tubes 212. The multi-segmented rods comprise a plurality of hinged or flex points 169 which define each segment of the multi-segmented rod. FIG. 26A illustrates a multi-segmented rod in a linear configuration. The rod can be bent at one or more flex point 169 to form a rod having an non-linear configuration as shown in FIG. 26B. A rod can be removeably positioned within a flexible tube 212. The flexible tube 212 can be attached in proximity to the distal portion of the central tube 106. As shown in FIG. 26D the linear configuration of the flexible tube is assumed when the segments of the distal tube are spaced. In this configuration, the multi-segmented rod can be passed into the tube in its linear configuration as shown in FIG. 26E. When the segments of rigid holey tubes are actuated and pulled together, they combine to create a longer rigid section of the central tube 106, the rod tube 212 and the multi-segmented rod assume a non-linear configuration as shown in FIG. 26F. Movement of the rod 211 and rod tube 212 into the non-linear configuration can move the enclosure into its expanded configuration. Similarly, movement of the rod 211 and rod tube 212 back into a linear configuration allows retraction of the enclosure. The expandable section can be inserted into a patient's organ or removed from the patient's organ in its non-expanded, or retracted, configuration. To increase flexibly of the device, which can preferably ease insertion or removal, the device can be inserted into the patient prior to inserting one or more rod 211 into the rod tubes 212, and the device can be removed from the patient after removal of one or more previously inserted rods.

As illustrated in FIG. 2B, the covering 113 of the expandable portion of the outer tube component distal to the containing ring 115 and extending vertically to the distal ends of the expansion rib tubes, is a flexible, impermeable material such as polyester film or plastic sheet.

When the distal end of the outer tube 100 is in its un-expanded (e.g. retracted) configuration, the covering 113 folds down to accommodate the smaller diameter of the component 100 as illustrated in FIG. 2A. When the distal end of the outer tube is in its expanded configuration, the covering 113 spreads to its designed shape creating an enclosure of a size encircling the central tube 106.

The bottom 114 of the distal end of the expanded outer tube 100 is covered with a permeable material such as nylon, elastane, cotton or other breathable fabric. The inner circumference of the permeable material on the bottom of the expandable section of the outer tube is connected to the upper perimeter of the distal holey tube section 107 and the outer circumference of the permeable material on the bottom of the expandable section of the outer tube is connected to the distal perimeter of the material covering 113 of the expanded enclosure.

When a vacuum is applied to the enclosure, the permeable material allows fluid communication of suction out of the bottom of the expanded enclosure. The permeable material 113 on the bottom of the expandable section also serves to cover and contain the distal ends of the receiving tubes 103 and the umbrella struts 117 of the outer tube's un-expanded configuration, thereby creating a smoother surface of that region of the device, thereby facilitating patient insertion.

As illustrated in FIG. 3A, the distal end of the suture delivery tube set component 101 is configured in its un-expanded (e.g. retracted or linear configuration). This retracted configuration facilitates insertion of the suture delivery tube set component 101 into and partially through the distal end of the outer tube component 100. This configuration also facilitates withdrawal of the suture delivery tube set component 101 from the outer tube component 100.

The delivery tubes 104 are bundled to run parallel to one another. The distal ends of the delivery tubes 104 are attached to warping cables 122. Each warping cable 122 passes through individual rigid tube segments 120 that are attached in spoke-like fashion to the delivery tube circumferential support platform 121. The warping cables 122 may pass through holes in the containment ring 119 and then run through a dedicated warping cable containment tube 123. The containment tube 123 optionally runs up the center of the delivery tube bundle as shown in FIG. 3A. However, the containment tube 123 may also provide a passage for the warping cables without being located in center of the delivery tube bundle. The warping cables are attached on their proximal end to a lever mechanism 161 that is contained within the activation handle 166 of the suture delivery tube set component 101 as illustrated later in FIGS. 20B and 20C.

When the activation handle 161 is actuated by the operator, the warping cables 122 pull the distal ends of the delivery tubes 104 thereby bending them outward. As the length of the warping cables 122 continue to shorten between the attachment points at the distal ends of the delivery tubes 104 and their point of passage through the containment ring 119, the delivery tubes will continue to bend until the distal ends of the delivery tubes make contact with the vertically concave ends of the rigid tube segments 120 of the delivery tube circumferential support platform 121 as illustrated in FIG. 3B. As further illustrated in FIG. 3B the distal ends of the reconfigured delivery tubes 104 are positioned so that they are parallel to the delivery tube bundle but now run in the opposing direction.

The delivery tube circumferential support platform 121 may be comprise a flexible impermeable material formed in a generally circular shape and is attached to the rigid tubes 120 which run radially from the platform's center in a spoke-like fashion. The delivery tube circumferential support platform 121 collapses to a tube-like configuration as illustrated in FIG. 3A, and when in its expanded configuration, to form a wheel-like configuration as illustrated in FIG. 3B and FIG. 3C. The flexible impermeable material folds and unfolds for facilitate the expansion and collapse of the platform 121. The flexible impermeable material of the delivery tube circumferential support platform 121 may be made of a material such as polyester film or plastic sheet. The platform also serves as the distal wall of the created suction enclosure of the device.

The circular shape of the platform 121 maintains the desired circumferential configuration and spacing of the delivery tubes 104 positioned around the platform's 121 perimeter. The rigid tubes 120 of the delivery tube circumferential support platform 121 are configured in their expanded configuration to fit into the notches 108 of the distal holey tube segment 107. A lower containment ring 124 is positioned around the delivery tube bundle distal to the inner circumference of the platform 121. The containment ring 119 has the ability to slide over the delivery tube bundle, such that when the expanded distal end of suture delivery tube set component is pulled proximally to couple with the expanded distal end of the outer tube component 100, the containment ring 119 slides down and maintains pressure against the lower containment ring 124 as pressure is applied from above by the slotted distal holey segment 108 of the outer tube component 106, thereby creating and maintaining a 90 degree relationship between the rigid tubes 120 of the platform 121 and the central tube 106 of the outer tube 100. This perpendicular relationship vertically aligns the delivery tubes 104 of the suture delivery tube set component 101 with the receiving tubes 103 of the outer tube component 100. The horizontal or circumferential alignment of the delivery tubes 104 and the receiving tubes 103 is managed by the coupling, or inserting the horizontal profile, of the radially expanded rigid tubes 120 into the slotted template 108 of the distal holey tube segment 107.

FIG. 3C illustrates aspects of an example system wherein the distal end of the suture delivery tube set component 101 comprises a proximal and a distal delivery tube circumferential support platform 121, 167. In this embodiment, the inner circumference attachment point to the containment ring 119 of the distal delivery tube circumferential support platform 167 is located a specific distance, for example 1.0 centimeter, distal from the inner circumference attachment point to the containment ring 119 of the proximal delivery tube circumferential support platform 121.

In this example, the delivery tubes 104 have a second set of warping cables 122 attached near their distal end located the same specific distance, for example 1.0 centimeter, distal to the attachment point of the first set of warping cables 122. The two platforms are equal in size, material, and construction. The two sets of warping cables 122 are actuated in unison such that the platforms expand in unison. The rigid tubes 120 of the two platforms 121, 167 are of the same length and are vertically aligned, thereby holding the delivery tubes 104 parallel to the containment ring 119, maintaining the pitch axis. The equidistant circumferential spacing of the rigid tubes 120 of the aligned two platforms 121, 167 maintains the roll axis of the delivery tubes 104.

Large diameter distal ends of the receiving tubes 103 are beneficial to the operation of the device 99 by increasing the margin for error related to the alignment of the delivery tube distal ends 104 with the receiving tube distal ends 103. When operating the device, the needles 139 are advanced out of the distal ends of the delivery tubes 104, and then must cross the suction gap 102 also referred to herein as circumferential gap, penetrating the drawn in tissue 153, as shown in FIGS. 25E and 25F, and subsequently enter the distal ends of the receiving tubes 103. The lack of suction port support struts across the gap enables a large circumferential bite of tissue, which can provide enhanced surgical results.

Figure 4A:
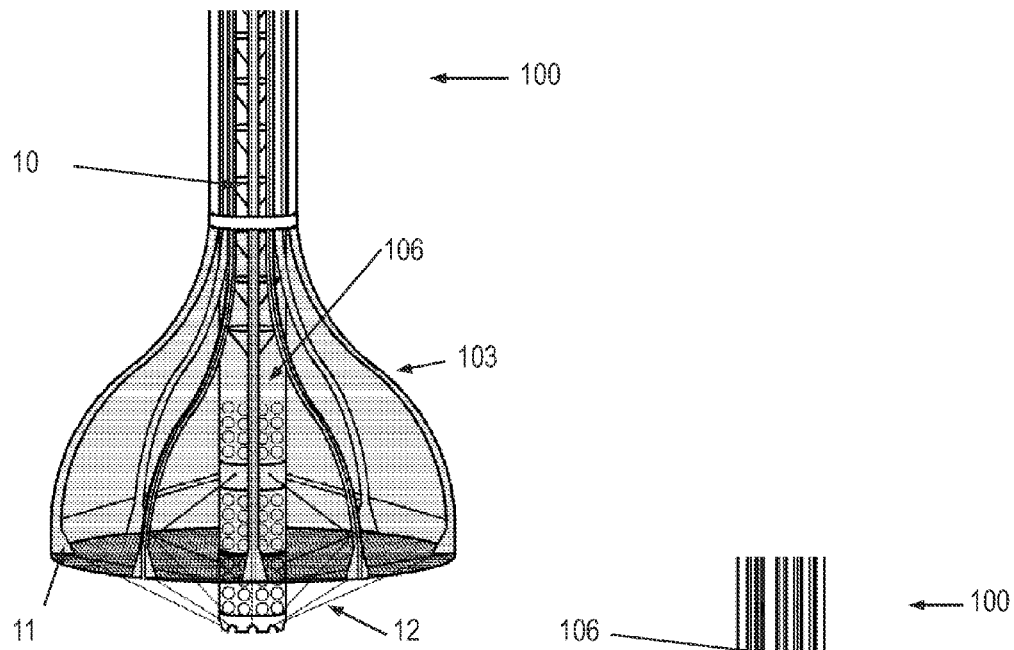
FIG. 4A is a schematic diagram illustrating a view an expanded outer tube component with funnels in the central lumen.
Figure 4B:
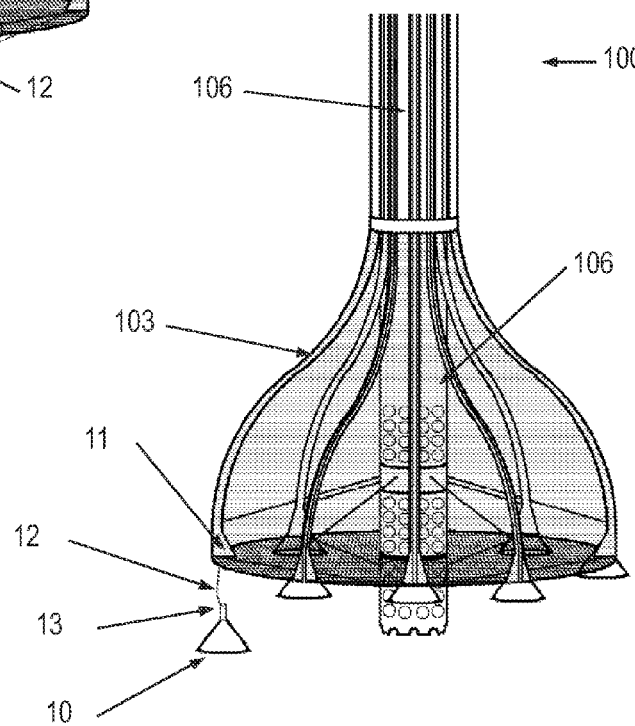
FIG. 4B is a schematic diagram illustrating a view an expanded outer tube component with funnels in the receiving tubes.

Forces applied to the device 99, such as torque, during the device's engagement with the tissue and subsequent deployment of suture needles, may somewhat misalign the relationship between the delivery tube distal ends 104 and the receiving tube distal ends 103. A receiving tube 103 with a large diameter at its distal end may reduce the possibility that a needle or needles 139 will fail to enter the corresponding receiving tube 103. The problem with having receiving tubes with large diameter distal ends is that they may increase the overall diameter of the device, thereby making the device too large and impractical to insert safely into a patient's natural orifice. FIG. 4A and 4B illustrates an example whereby the distal ends of the receiving tubes 103 increase their diameters by remotely adding funneled tips 105 subsequent to the outer tube component's 100 insertion into a patient.

The component nature of the present invention enables parts of the device to assemble and disassemble inside the patient. The component nature of the device allows it to be less rigid at the time of insertion and withdrawal and also allows a device with a smaller diameter thereby facilitating patient insertion.

Individual funnels 105 are incorporated with lengths of threads 125. The proximal end of the threads 125 may be attached to wires, not pictured, which may facilitate the threading of the threads 125 through the distal end of the receiving tubes 104. The distal end of the threads 125, which are incorporated with the funnels 105 are temporarily positioned within the lumen of the central tube 106 so that the funnel necks 134 are pointed toward the distal end of the outer tube component 100.

A thread or string 157 may be threaded through at least the first funnel, subsequently passing both ends of the thread up and out of the proximal end of the outer tube component 100, thereby allowing an operator, or clamp/suture holder 148, to hold tension on the most distal funnel, thereby preventing the series of funnels from falling back out of the distal end of the outer tube. The outer tube is inserted into the patient with the funnels held within the lumen of the central tube 106.

Once the distal end of the outer tube is positioned within the stomach, the operator may release one end of the funnel maintaining 157 thread then remove the maintaining thread from the proximal end of the outer tube 100. The operator my now pull the proximal ends of the funnel threads 125 thereby advancing the series of funnels 105 down and out of the lumen of the central tube 106.

An endoscope or endoscopic device may assist in pushing the series of funnels 105 out of the distal end of the central tube 106. The endoscope may now inspect the stomach and determine visually if the outer tube component 100 is in the proper location in preparation for the expansion of the outer tube component 100.

Mild tension is maintained on the funnel threads 125 as to keep the threads 125 and funnels 105 in relative position as the distal end of the outer tube component 100 is expanded. Subsequent to expansion of outer tube's distal end, the funnel threads 125 are pulled by the operator until the funnel necks 134 are each fully inserted into the distal end of their corresponding receiving tubes 103 as illustrated in FIG. 4B.

A retroflexed endoscope can visually confirm the position of the funnels 105. When the funnel 105 incorporation with the receiving tubes 103 is confirmed, the funnel threads 125 are secured on the outside of the proximal end of the outer tube component 100, thereby holding them in place. The funnels 105 will remain in place during suture deployment and can be removed after the suture delivery tube set component 101 and outer tube component 100 have been withdrawn from the patient.

Subsequent to the removal of the outer tube component 100, the funnels 105 remain encircling each suture arm of the deployed sutures 128 which run from the point of tissue incorporation, upward and out of the patient's body. The funnel threads 125 and their attached funnels 105 may be removed from the patient by simply pulling each thread with attached funnel individually up and out of the patient and subsequently off the distal end of the suture needle 139.

Figures 5A, 5B:
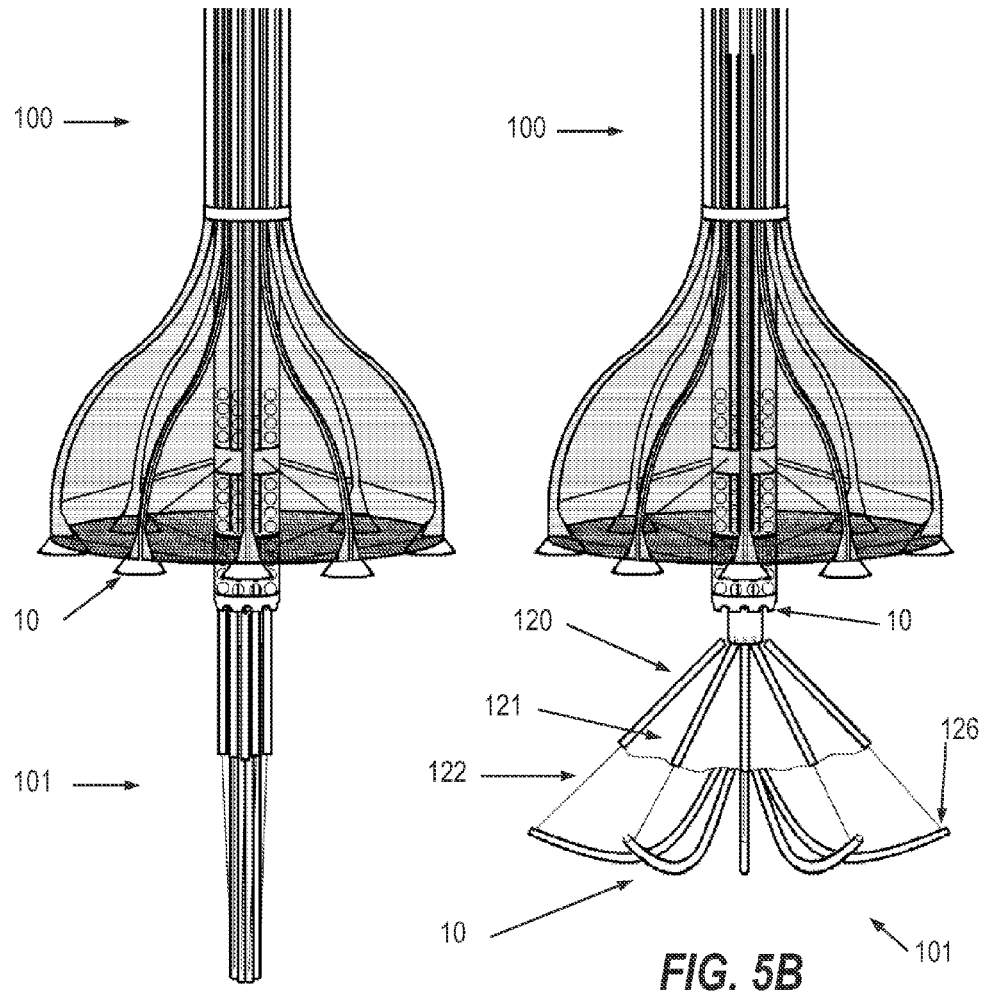
FIG. 5A is a schematic diagram illustrating a view of an expanded outer tube component incorporated with an un-expanded suture delivery tube set component.
FIG. 5B is a schematic diagram illustrating a view of an expanded outer tube component incorporated with a partially expanded suture delivery tube set component.

FIG. 5A illustrates the expanded outer tube component 100 with receiving funnels 105 deployed and with the suture delivery tube set component 101 inserted through the distal end of the outer tube component 100 in its linear or unexpanded configuration.

FIG. 5B illustrates the expanded outer tube component 100 with receiving funnels 105 deployed and with the suture delivery tube set component 101 inserted through the distal end of the outer tube component 100 with its distal end in a partially expanded configuration. This figure illustrates the formation of the delivery tube circumferential support platform 121 as the warping cables 122 bend the delivery tubes 104. Subsequent to the complete actuation of the warping cables 122, the reconfigured distal end of the suture delivery tube set component 101 is raised and locked into position such that the spoke-like rigid tubes 120 of the platform 121 are fitted into the notches 108 of the distal end of the outer tube's central tube 106 as described earlier.

FIGS. 6A, 6B, and 6C illustrate an example related to loading, maintaining, and positioning a distal ring graft 127 on the distal end of the suture delivery tube set component 101. The distal ring graft 127 may be loaded, or incorporated with the suture delivery tube set component 101 in several fashions.

In the example illustrated, the distal ring graft 127 is directly attached to or incorporated with a plurality of sutures 128 attached to needles 139. The plurality of needles 139 are advanced, needle tip first, up the distal ends of the delivery tubes 104, matching the circumferential order of suture attachment to the ring graft 127 to the circumferential order of the delivery tubes 104 as they are bundled in the suture delivery tube set component 101.

The needles 139, after completely passing through the delivery tubes 104, are then turned around and advanced down the proximal end of the delivery tubes 104, running parallel to their attached sutures 128, to a point where the needle tips 139 are contained in the distal end of the delivery tubes 104. The ring graft 127 may then be raised, encircling the suture delivery tube set component 101, to a position proximal to the un-expanded delivery tube circumferential support platform 121, as illustrated in FIG. 6A.

A tension maintenance string 156 may be looped through the ring 127 and held by the operator, or a clamp/suture holder 148, on the proximal end of the suture delivery tube set component 101 as illustrated in FIG. 6B. Tension is maintained on the tension maintenance string 156 during the reconfiguration of the distal suture delivery tube set platform 121. Subsequent to the distal end of the suture delivery tube set component's reconfiguration, tension is released on the tension maintenance string 156, and by letting go of one arm of the looped string, it can be withdrawn from the ring. The operator pulls the suture's 128 slack at the proximal end of the suture delivery tube set component 101, thereby pulling the distal ring graft 127 into position above the expanded delivery tube circumferential support platform 121 as illustrated in FIG. 6C.

In another example, the distal ring graft 127 directly attached to sutures 128 is loaded into the distal end of the suture delivery tube set component 101 as described earlier, but instead of maintaining the ring graft 127 with a graft maintenance string 156 within the central tube 106 of the outer tube component 100, the distal ring graft 127 is maintained proximal to the proximal end of outer tube's central tube 106.

In this example, the proximally maintained ring graft 127 encircles the suture delivery tube set component's delivery tubes 104 and the attached sutures run the down the length of the delivery tubes 104 within the lumen of the central tube 106, then radiate out the bottom of the central tube 106 and enter the distal ends of the corresponding bent delivery tube 104 of which each suture 128 was loaded.

The attached suture 128 is optionally of a length at least as long as combined length of the delivery tubes 104, the vertical distance of the suction gap 102, and the length of the receiving tubes 103. Subsequent to the deployment of the suture needles 139 and withdrawal of the suture delivery tube set component 101, the sutures 128 are pulled from the proximal end of the receiving tubes 103, which pulls the distal ring graft 127 down the central tube 106 of the outer tube component 100 until it emerges out of the distal end of the central tube of the outer tube within the stomach. The distal graft is now in position and ready to be fixed to a proximal graft 142. This embodiment enables the use of grafts of a size that are too large to fit within the central tube 106 of the outer tube 100 when the suture delivery tube set component 101 is also contained within the central tube 106 of the outer tube component 100.

Figures 7A, 7B:
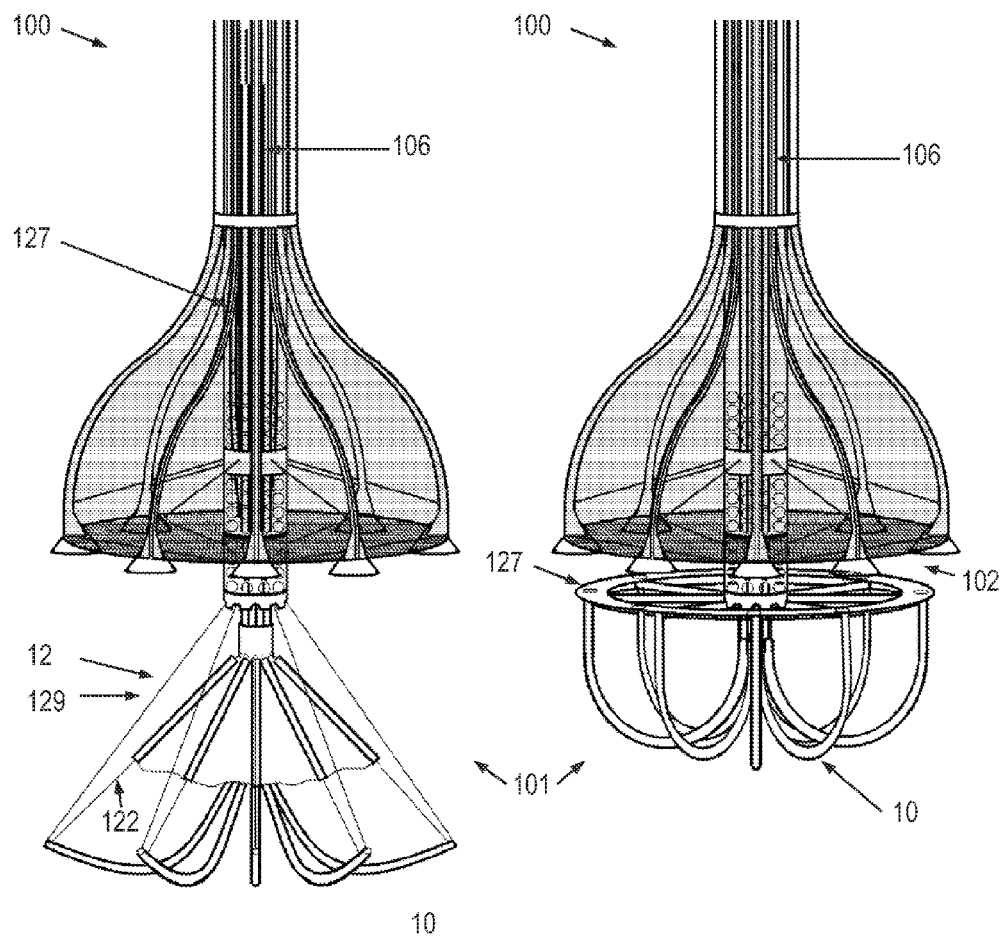
FIG. 7A is a schematic diagram illustrating a view of an expanded outer tube component incorporated with a partially expanded suture delivery tube set component incorporated with a partially positioned ring graft.
FIG. 7B is a schematic diagram illustrating a view of an expanded outer tube component incorporated with a partially expanded suture delivery tube set component incorporated with a ring graft positioned for deployment.

FIGS. 7A and 7B illustrate the procedure described above with the expanded outer tube component in place. In another example, instead of the ring graft being directly attached to sutures, the ring graft is directly attached to ring graft maintaining threads 129. Instead of the directly attached sutures holding the ring graft 127 in place above the platform 121, ring graft maintaining threads 129 run through distal ends of the suture delivery tube set component's 101 delivery tubes 104 and are secured on the proximal end of the component as described earlier for the previously described direct attachment of suture to ring embodiment. In a further example, the ring graft maintaining threads 129 may be passed through dedicated tubes or channels 130 running parallel to the suture delivery tubes. These tubes or channels 130 will be described in further detail in FIGS. 13A, 13B, and 13C.

Independent sutures 128 with suture anchors 140 are optionally utilized to pass through the body of the ring graft 127 as it is held in place above the distal ends of the delivery tubes 104. This eliminates the need to have the suture needle 139 run parallel to its attached suture 128 within the delivery tube 104, thereby eliminating the task of maintaining the suture's 128 slack.

Figure 8A:
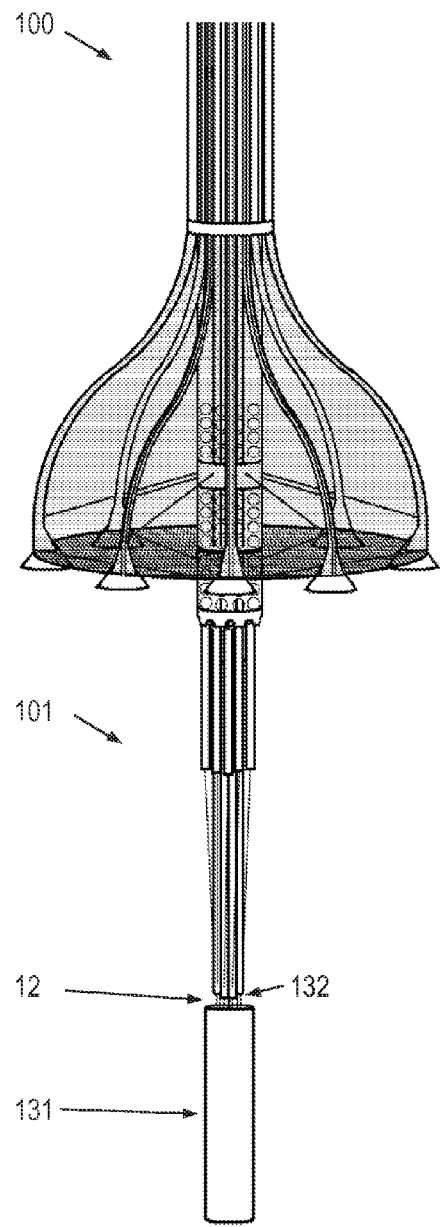
FIG. 8A is a schematic diagram illustrating a view of an expanded outer tube component incorporated with an un-expanded suture delivery tube set component with a distal ring holder.
Figure 8B:
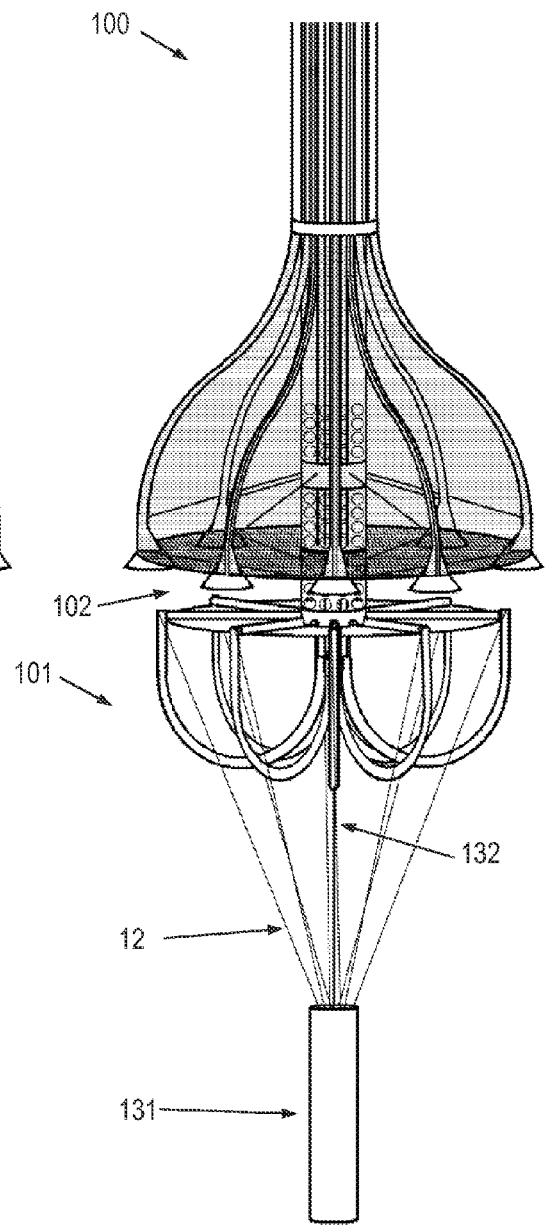
FIG. 8B is a schematic diagram illustrating a view of an expanded outer tube component incorporated with an expanded suture delivery tube set component with a distal ring holder.

FIGS. 8A and 8B illustrate a further embodiment for maintaining the distal graft 127 prior to deployment and implantation. A distal graft holder 131 is attached to a flexible wire 132 and is contained within the suture delivery tube set component 101. The distal graft holder 131 is a hollow tube that may releasable hold the graft 127 in place distal to the distal end of the delivery tubes 104. This embodiment may be utilized when a large graft, such as a tube shaped graft, is to be implanted.

FIG. 9 illustrates a series of stiffening wires 112 and a segment view of the outer tube component 100. The series of stiffening wires 112 may be made of a flexible metal wire. In the present invention, a material with shape memory, such as Nitinol is preferred. The series of stiffening wires 112 may be attached to each other as a unit as illustrated in FIG. 9, or alternatively, they may simply be individual wires placed independently. The stiffening wires 112 are sized to fit into the expansion rib tubes 111.

The outer tube component may be inserted into the patient without the stiffening wires contained in the expansion rib tubes 111. This enhances the flexibility of the outer tube component and facilitates insertion into the patient through the patient's mouth. Subsequent insertion of the stiffening wires 112 into the expansion rib tubes 111 is simple and atraumatic to the parts of the patient's throat and upper digestive and system. The stiffening wires 112 contained in the expansion rib tubes 111 enables the structure and stability of the umbrella function of the expandable section of the distal outer tube component 100 when the umbrella struts 117 are actuated by the operator. The stiffening wires 112 may be removed from the expansion rib tubes 111 subsequent to suture deployment and prior to withdrawal of the outer tube component 100 from the patient.

FIGS. 10A and 10B illustrate a cross sectional view of the bottom distal end of the expanded outer tube component 100 with releasably held funnels 105 in place. The complete diameter of the funneled distal ends of the receiving tubes is optionally contained within the perimeter of the expanded distal end of the outer tube component 100 as illustrated in FIG. 10A and FIG. 10B. The radial expansion of the umbrella struts 117 is illustrated. The bottom distal covering 114 of the expanded distal end of the outer tube component 100 with a permeable fabric is illustrated as well. This permeable fabric covering 114 allows suction to communicate through it. The permeable fabric 114 restrains and controls the amount and distribution of acquired tissue drawn into the suction gap 102 of the device 99.

FIG. 10B illustrates an embodiment of the present invention wherein the outer tube component 100 has twice, or other multiple, the number of receiving tubes 103 as the suture delivery tube set component 101 has delivery tubes 104. In this embodiment, in use, the operator deploys a series of suture needles 139 attached to sutures 128 with suture anchors 140 through a distal graft 127 and the acquired tissue 153 within the suction gap 102 of the device 99.

Tension is maintained on the deployed sutures on the proximal end of the outer tube component 100, the distal end of the suture delivery tube set component 101 is remotely reconfigured into its linear configuration, a second series of suture needles 139 attached to sutures 128 with suture anchors 140 are advanced into the proximal end of the suture delivery tube set component 101 such that the needle's distal points are contained in the distal end of the delivery tubes 104, the distal end of the suture delivery tube set component 101 is remotely reconfigured into its circumferential deployment configuration, the delivery tube circumferential support platform 121 is rotated one notch 108 from its previously coupled location and re-coupled with the outer tube component 100, and the second series of suture needles 139 attached to sutures 128 with suture anchors 140 is deployed into the second set of receiving tubes 104. In this embodiment, the notched end of the distal holey segment 108 has twice the number of notches as there are delivery tubes 104. Subsequently, the procedure continues in a fashion similar to the procedure where only one series of sutures are deployed.

FIGS. 11A, 11B, and 11C illustrate example features and deployment aspects of the receiving tube funnel tip components 105. The benefits of having funneled receiving tubes have been described earlier. FIG. 11A illustrates how a series of funnels 105 may be advanced through the central lumen of outer tube component 100. A funnel tension string 157 may be looped through at least the first funnel and held by the operator, or clamp/suture holder 149, as the over tube component 100 is inserted into the patient, thereby maintaining the funnel series within the tube 106. Releasing one end of the funnel tension string 157 and removing the string from the proximal end of the outer tube component 100 releases the funnels 105 enabling their further deployment as described earlier.

FIG. 11B illustrates a partially deployed funnel 105 being pulled into the distal end of a receiving tube 103 by the attached funnel thread 125. The distal end of the receiving tube 103 has a funnel configuration 118 to aid in the mating and stabilization of the funnel 105 to receiving tube 103 connection. The funnel neck 134 is of a length that further enhances stabilization of the funnel 105 within the receiving tube distal end 103 by simple means of containment. The funnels 105 are optionally made of a hard material such as stainless steel, titanium, Nitinol, or plastic.

The angled internal sides of the funnels 105 deflect and steer the flexible needle tips 139 up into and through the funnel neck 134, thereby allowing its advancement into and through the receiving tubes 103. The funnels 105 have a diameter of a size that is able to pass freely through the central lumen of the outer tube. Optionally, the diameters of funnels are approximately 10.0 millimeters. Optionally, the funnels 105 are made of a material with shape memory and configured to expand from one diameter size to a larger diameter size when deployed out of the central tube and into their fully deployed positions.

FIG. 11C illustrates a funnel 105 fully deployed into and coupled with a receiving tube distal end 103. The funnel 105 is held in place by tension on the funnel thread 125 which is secured on the proximal end of the outer tube component 100. When the sutures 128 have been deployed, the distal ends of the funnel threads 125 are released and the outer tube component 100 is withdrawn from the patient with the funnel threads 125 flowing out of the distal ends of the receiving tubes 103. The funnel threads 125 may subsequently be grasped by the operator and pulled up and out of the patient as described earlier.

Figure 12A:
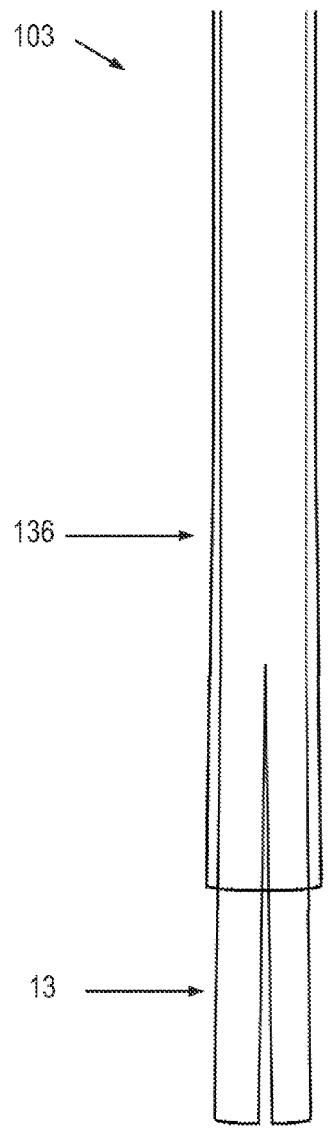
FIG. 12A is a schematic diagram illustrating a view of an un-deployed receiving tube distal end.
Figure 12B:
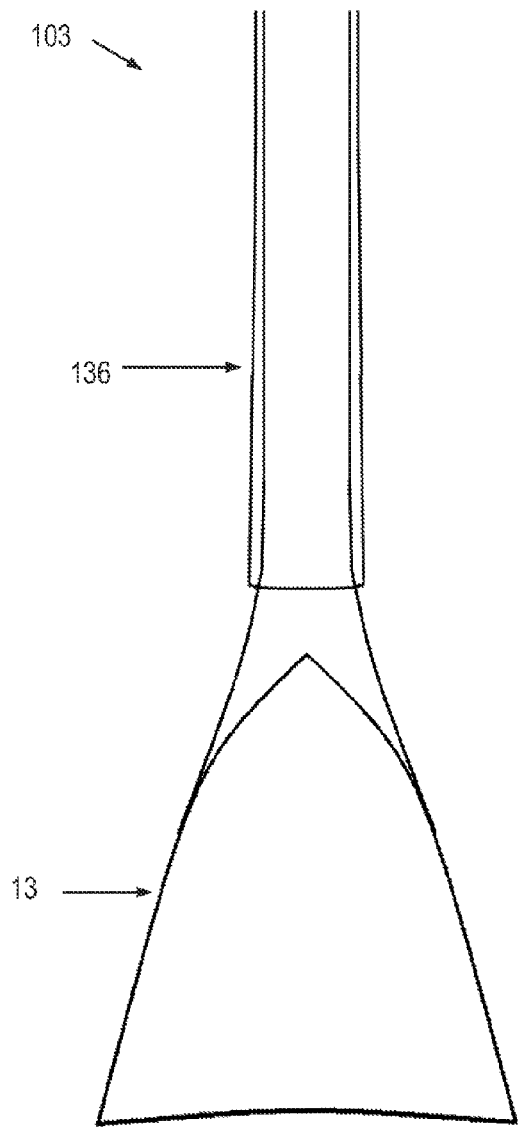
FIG. 12B is a schematic diagram illustrating a view of a deployed receiving tube distal end.

FIGS. 12A and 12B illustrate an example alternate means of increasing the diameter of the distal ends of the receiving tubes 103. In this embodiment, the distal end of the receiving tube 103 is made of a material which has shape memory. The distal end of the receiving tube 103 is formed from a funnel which has been splayed vertically on its distal end. The splayed funnel 135 is configured to have a splayed configuration when the distal end is not contained within a sheath 136. When the outer tube component 100 is in its expanded configuration, the splayed funnel tip 135 is out of its sheath 136 and held against the wall of the suction enclosure 113. When the outer tube component 100 is in its un-expanded configuration, the splayed funnel tip 135 is contained within the sheath 136. An operator is able to remotely actuate the vertical movement of the splayed funnel tip 135 within the sheath 136.

Figure 13A:
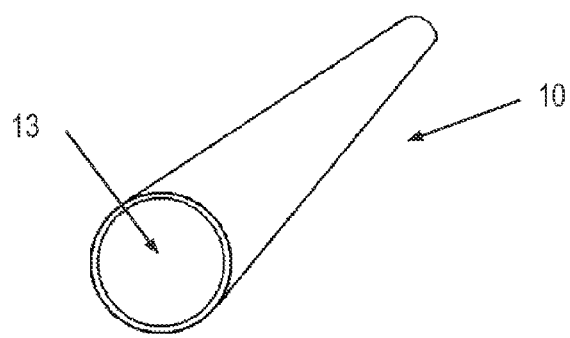
FIG. 13A is a schematic diagram illustrating a view of a segment of a delivery tube.
Figure 13B:
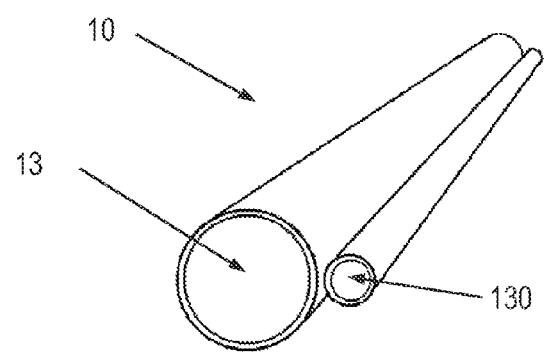
FIG. 13B is a schematic diagram illustrating a view of a segment of a delivery tube coupled with a retaining tube.
Figure 13C:
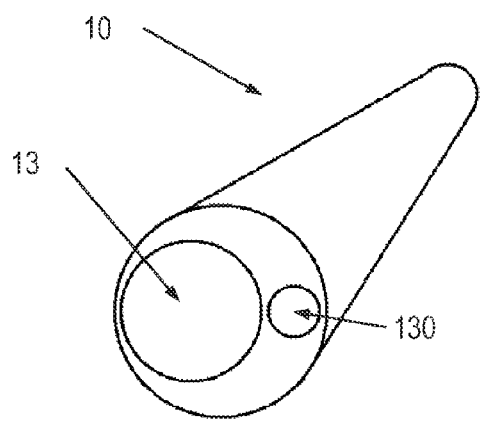
FIG. 13C is a schematic diagram illustrating a view of a segment of a delivery tube incorporated with a retaining tube.

FIGS. 13A, 13B, and 13C illustrate sectional views of three different configurations of the delivery tubes 104. 13A illustrates a delivery tube section with a single central bore 138. The tube is optionally made of a flexible material such as stainless steel, braided extruded plastic, polyimide, PEEK, PTFE, EPTFE, or other flexible tubing material.

The flexible needle 139 of the device passes through the tubing and follows a path which is determined by the configuration of the tubing. FIG. 13B illustrates a delivery tube section 104 comprised of a first main tube with a bore 138 for the passage of needles and suture, and a second smaller tube attached and running parallel such that the first larger bore tube 138 is connected side to side to the second smaller bore 130 tube. The second smaller bore tubes 130 temporarily contain the ring graft maintaining threads 129 which position the ring graft in place within the suction enclosure and then maintains the position of the ring graft 127 during deployment of the sutures 128. FIG. 13C illustrates a delivery tube section 104 which serves in function similar to the previously described tube, but in this embodiment, the single tube is formed with two bores of channels within its cross sectional circumference.

The long flexible needles 139 are of a length that is at least as long as the combined length of the delivery tube 104, receiving tube 103, and the suction gap 102. This length enables the operator to push the needle 139 through the delivery tube 104, traverse the suction gap 102, enter, travel through, and exit the receiving tube 103, where the operator can grasp the distal end of the needle 139 and pull it completely through the delivery and receiving tubes of the device 99.

Figures 14A, 14B:
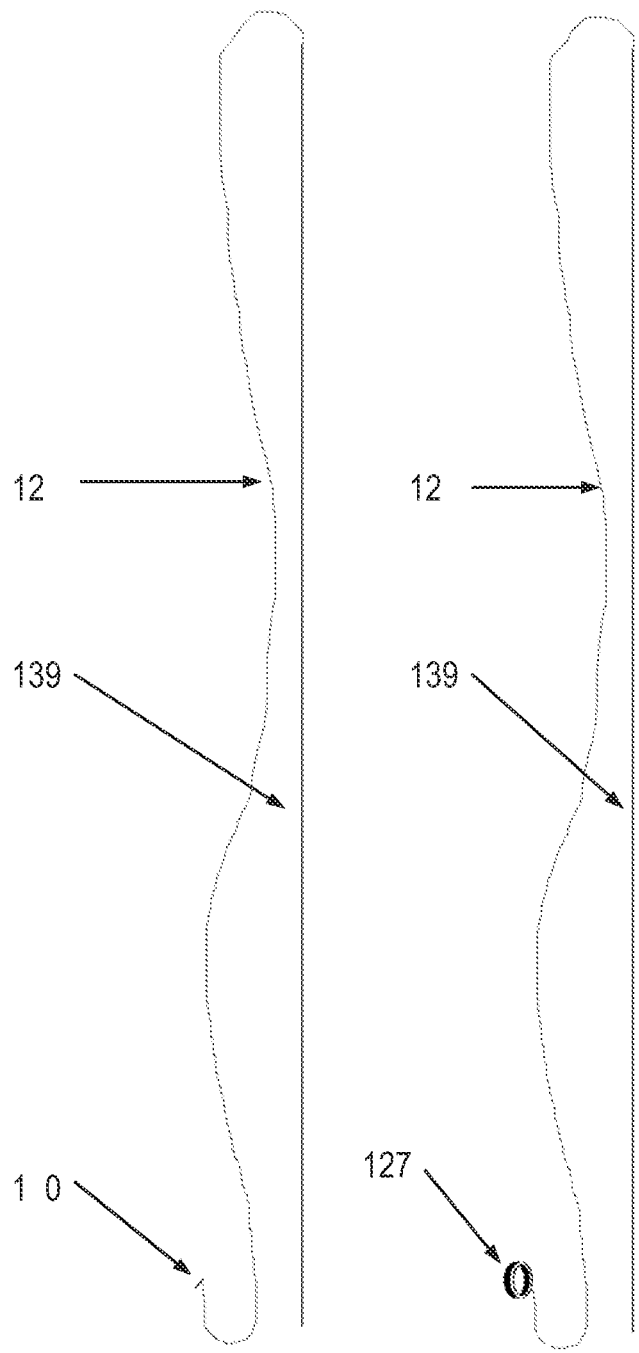
FIG. 14A is a schematic diagram illustrating a view of a needle incorporated with a suture and suture anchor.
FIG. 14B is a schematic diagram illustrating a view of a needle incorporated with a suture attached to a ring graft.

FIG. 14A illustrates a long flexible needle 139 attached to a suture 128 which is attached to a suture anchor 140. The suture 128 is optionally at least as long as the combined length of the receiving tube 103 and the length of the suction gap 102. Optionally, the needle 139 is pushed forward though the delivery tubes 104 and receiving tubes 103 with the suture 128 and the suture anchor 140 trailing behind it. The suture anchor 140 is of a size and configuration such that it can pass through the delivery tube 104. When the suture has advanced through the tubes such that the suture anchor 140 is in or near the distal end of the warped delivery tube 104, the operator may remotely reconfigure the distal end of the suture delivery tube set component 101 thereby enabling the suture anchor 140 to exit the distal end of the delivery tube 104. The suture anchor 140 is of such a size and configuration that it will not pass through the body of a graft or through a plication of tissue.

FIG. 14B illustrates a long flexible needle 139 attached to a suture 128 which is attached to a distal ring graft 127. Optionally, the suture 128 is at least as long as the combined length of the delivery tube 104, receiving tube 103, and the suction gap 102. The needle 139 is loaded into the delivery tube 104 such that the needle runs parallel to its attached suture 128 with the distal tip of the needle positioned in the distal end of the delivery tube 104. The delivery tubes of the device can be loaded with needles in their linear configuration, thereby simplifying the loading process. The delivery tubes can be reloaded with needles in situ.

When the distal end of the delivery tube 104 is warped into its deployment configuration, the distal end of the needle 139 is also warped, thereby eliminating the need to push the needle tip 139 through the bend in the delivery tube 104. With the needle tip already past the bend in the delivery tube, the needle advances easily through the delivery tube 104. When advancing the needle in this example, tension is maintained on the suture slack running parallel to the needle.

A loop of thread through the loop of the suture slack enables the operator to maintain tension of the suture slack until the suture loop reaches the distal end of the delivery tube 104, at which point the operator releases one end of the tension retaining thread and withdraws it from the proximal end of the delivery tube 104, thereby releasing the suture slack loop.

Figures 15A, 15B:
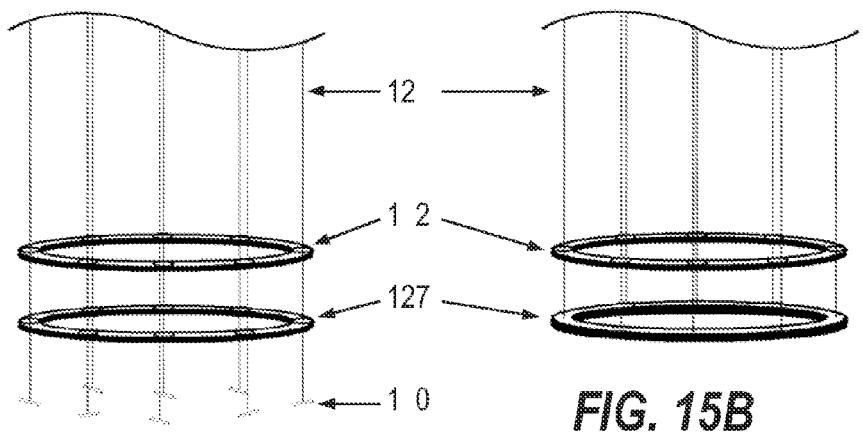
FIG. 15A is a schematic diagram illustrating a view of a set of same size ring grafts incorporated with suture with suture anchors.
FIG. 15B illustrates a view of a set of same size ring grafts incorporated with sutures.

FIGS. 15A-15F illustrate example ring graft 127 and 142 configurations. FIG. 15A illustrates use of a distal ring graft 127 that is held in place on the distal side of the suction gap 102 and subsequently having the ring graft body penetrated by the suture needles 139 with attached sutures 128 with attached suture anchors 140. Subsequent to suture delivery tube set component, outer tube component, and funnel series withdrawal from the patient, the proximal ring 142 is incorporated with the sutures 128, parachuted into position, and secured. Optionally, the suture needles penetrate apertures in the body of the ring. Optionally, the suture needles penetrate the body of the ring itself. In both examples, the suture anchor is prevented from passing completely through the ring body.

FIG. 15B illustrates an example utilizing a distal ring graft 127 that is directly connected to sutures 128 and is either; 1) held in place on the distal side of the suction gap 102, 2) held in a distal ring holder 131, or 3) held within the central tube 106 of the outer tube 100. Subsequent to suture deployment and subsequent suture delivery tube set component 101, outer tube component 100, and funnel 105 series withdrawal from the patient, the proximal ring 142 is incorporated with the sutures, parachuted into position and secured.

Figures 15C, 15D:
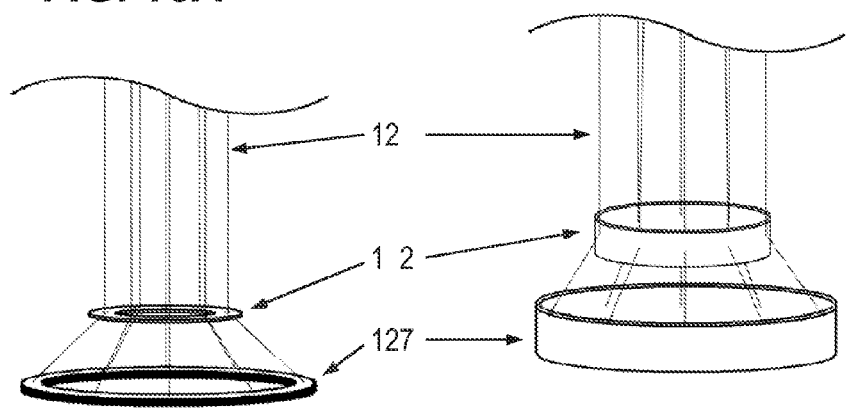
FIG. 15C is a schematic diagram illustrating a view of a set of dissimilar size ring grafts incorporated with sutures.
FIG. 15D is a schematic diagram illustrating a view of a set of dissimilar size ring grafts incorporated with sutures.

FIG. 15C illustrates an example similar to the one illustrated in FIG. 15B, but incorporates a proximal ring graft 142 of a smaller size relative to the distal ring graft 127. This mismatch in ring size enables a specific tissue augmentation configuration which may enhance durability and efficacy of the surgical procedure.

FIG. 15D illustrates an example similar to the one illustrated in FIG. 15C, but incorporates ring grafts that have a vertical band configuration that align securely with the configuration of the augmented tissue in this embodiment.

Figure 15E:
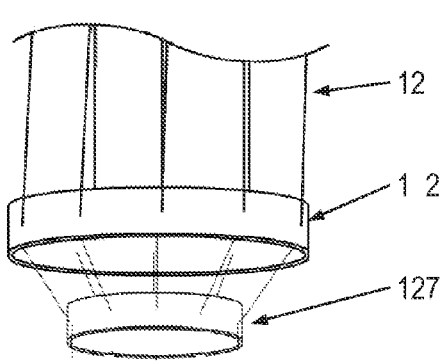
FIG. 15E is a schematic diagram illustrating a view of a set of dissimilar size ring grafts incorporated with sutures.

FIG. 15E illustrates an example where the proximal ring graft 142 is of a larger size relative to the distal ring graft 127. In this embodiment the relatively smaller distal ring graft 127 that is directly connected to sutures 128 and is either; 1) held in place in the center of the platform 121 on the distal side of the suction gap 102, 2) held in a distal ring holder 131, or 3) held within the central tube 106 of the outer tube 100. This mismatch in ring size enables a specific tissue augmentation configuration which may enhance durability and efficacy of the surgical procedure.

Figure 15F:
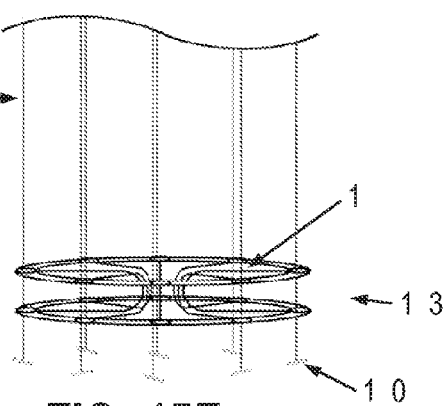
FIG. 15F is a schematic diagram illustrating a view of a double ring graft incorporated with sutures with suture anchors.

FIG. 15F illustrates an example where the distal ring graft 127 and the proximal ring graft 142 are connected by horizontal U-shaped struts 144 thereby creating a single implant unit 143. The horizontal U-shaped struts 144 are made of a flexible material with shape memory. Optionally, the double ring implant unit 143 is folded down, or compressed, and pulled and or pushed into position through the central channel 106 of the outer tube component 100 and held in position by ring graft maintaining threads 129 to the bottom of the expanded outer tube component 100.

Individual funnels 105 are slid on each ring graft maintaining thread 129 in order to provide the benefits of the larger diameter on the distal end of the receiving tubes 103. The suture delivery tube set component 101 passes through the central lumen 106 of outer tube component 100 and through the lumen of the releasably held double ring implant unit 143. The distal end of the suture delivery tube set component 101 is reconfigured and coupled to the outer tube component 100 as described earlier. The distal ring of the double ring implant unit is positioned directly above the distal ends of the platform. Suction applied to the expanded outer tube component 100 draws tissue into the circumference of the suction gap 102 which contains the horizontal U-shaped struts 144 of the double ring implant unit 143, thereby drawing tissue into the concavity of the U-shaped struts 144 of the double ring implant unit 143. Subsequently the needles 139 attached to sutures 128 which are attached to suture anchors 140 may now be actuated and secured as described earlier.

Figure 16A:
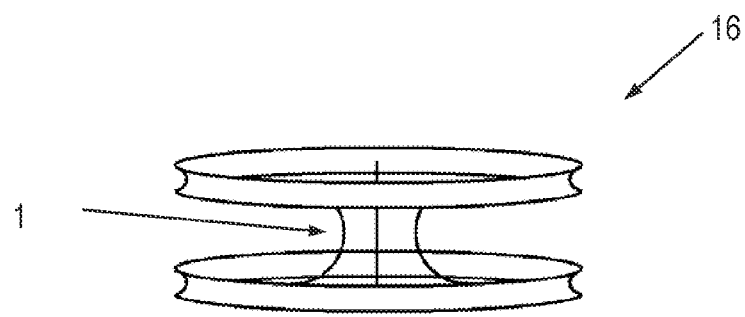
FIG. 16A is a schematic diagram illustrating a double ring stent.
Figure 16B:
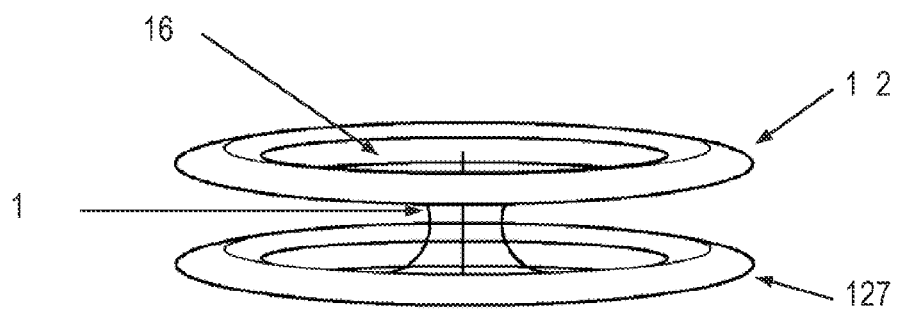
FIG. 16B is a schematic diagram illustrating a double ring stent with temporarily mounted ring grafts.

FIG. 16A and 16B illustrates the flexible rings 127, 142 which may optionally be temporarily supported on a flexible stent 168 in order to facilitate their positioning during tissue invagination and suture deployment. The flexible stent 168 is made of a material with shape memory. The stent has U-shaped struts 144 that allow tissue to be drawn into its circumferential concavity. Subsequent to securing the rings 127, 142 in tissue, the flexible stent may be detached from the rings and removed from the patient. The stent may be attached to the rings 127, 142 by being of a size that releasably holds the rings by means of the tension or a stretch fit, and or, by being temporarily sewn to the rings 127, 142 with threads that may be subsequently cut to release the rings. This is known to those skilled in the art of heart valve replacement and heart valve repair surgery, as the prosthetic cardiac valves and annuloplasty rings are temporarily mounted with thread to valve and ring holders.

Figure 17:
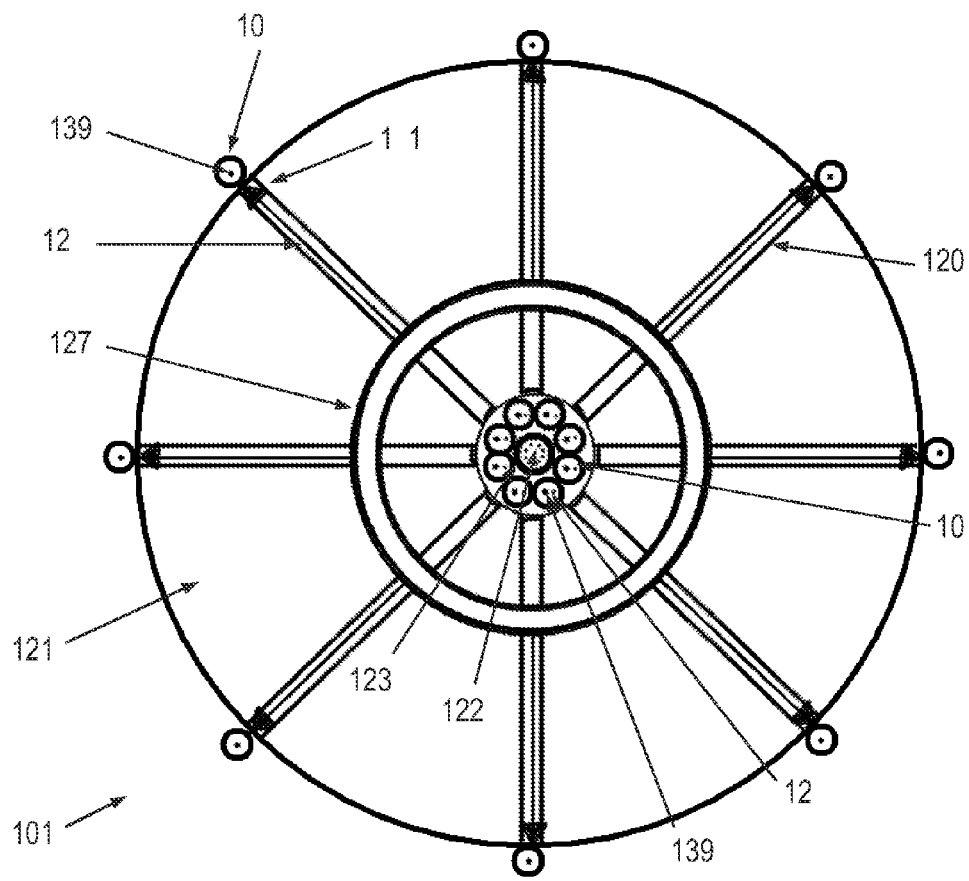
FIG. 17 is a schematic diagram illustrating a top sectional view of an expanded suture delivery tube set incorporated with a ring graft.

FIG. 17 illustrates a top sectional view of the expanded delivery tube circumferential support platform 121 incorporating a distal ring graft 127 having a diameter smaller than that of the platform 121. This ring size and deployment configuration enables a ring-to-ring implant configuration such as the one illustrated in FIG. 15E.

The distal ring graft 127 is maintained in the center of the platform 121 by the directly attached sutures 128 which extend from the ring 127 into the distal ends of the delivery tubes 104. Optionally, the sutures 128 incorporate spurs 151 which are able to pass through tissue and the body of the proximal ring graft 142 in a forward direction, but are unable to pass through the proximal ring 142 in a reverse direction subsequent to its penetration through the designed apertures of the proximal ring 142. FIG. 17 illustrates the position of the needle tips 139 at the distal end of the bent delivery tubes 104 as well as their position inside the length of delivery tubes 104 running up the central lumen of the outer tube component 100.

Figure 18:
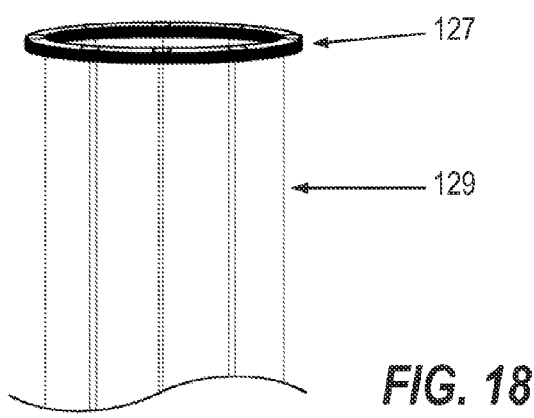
FIG. 18 is a schematic diagram illustrating a view of a ring graft incorporated with retaining threads.

FIG. 18 illustrates a distal ring graft 127 that is directly attached to graft maintenance threads 129. The threads 129 are attached to wires, not pictured, to facilitate the passage of the threads through either the delivery tube's lumen 138 or the dedicated tube or channel 130 for the graft maintenance threads 129. The graft maintenance threads 129 enable the ring to be positioned for insertion into the central lumen of the outer tube 106 with the ring 127 encircling the suture delivery tube set component 101 at a point proximal to the un-expanded platform 121, and subsequently enable the positioning of the ring 127 into position proximal to the distal ends of the reconfigured delivery tubes 104 by pulling the proximal ends of the graft maintenance threads 129 from the distal end of the suture delivery tube set component 101 and then securing the threads 129 in position with a clamp/suture holder 148 at the distal end of the suture delivery tube set component 101.

Subsequent to deployment of the sutures 128 through the ring 127 and drawn in tissue, the proximal ends of the graft maintenance threads 129 are released, allowing them to flow out of the distal ends of the delivery tubes 104, or dedicated tubes or channels 130, as the suture delivery tube set component 101 is withdrawn from the outer tube component 100. The graft maintenance threads 129 may be subsequently cut from the distal ring 127 using endoscopic instrumentation. Alternatively, they may be utilized to attach additional prostheses to the distal ring graft 127, for example a tube graft used for extending distally into the small intestine, a tube graft for extending proximally into the esophagus, or a suspended impeding component for slowing the passage of ingested food.

Figure 19:
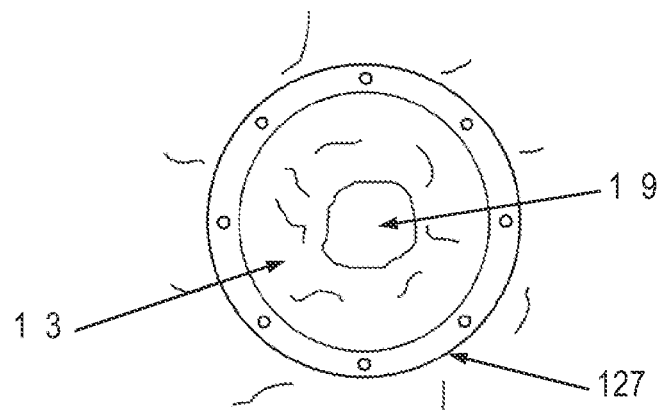
FIG. 19 is a schematic diagram illustrating a view of a ring graft incorporated in tissue.

FIG. 19 illustrates a view of an implanted ring graft 127 with a circumferential plication of tissue 153 incorporated within the lumen of the ring graft 127 which is secured to a second ring graft 142 on the opposite side of the tissue plication. The orifice 159 created is of a diameter size that is effective for slowing the passage of ingested food.

Figure 20:
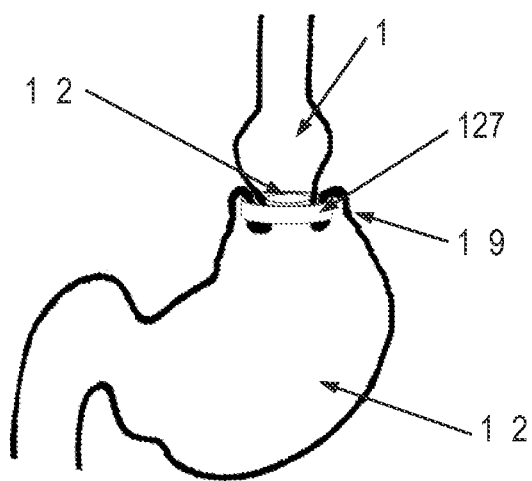
FIG. 20 is a schematic diagram illustrating a sectional view of a set of ring grafts incorporated in a stomach.

FIG. 20 illustrated a view of a stomach 152 with a constriction created in the proximal stomach by the implantation of a distal 127 and proximal ring graft 142. The configuration of the illustrated stomach constriction is produced with a relatively smaller proximal ring graft 142 secured to a relatively larger distal ring graft 127, such that the distal ring graft 127 surrounds the incorporated tissue 153 and the attached proximal ring graft 142. A small stomach pouch 154 is created proximal to the implanted ring grafts.

Figures 21A, 21B, 21C:
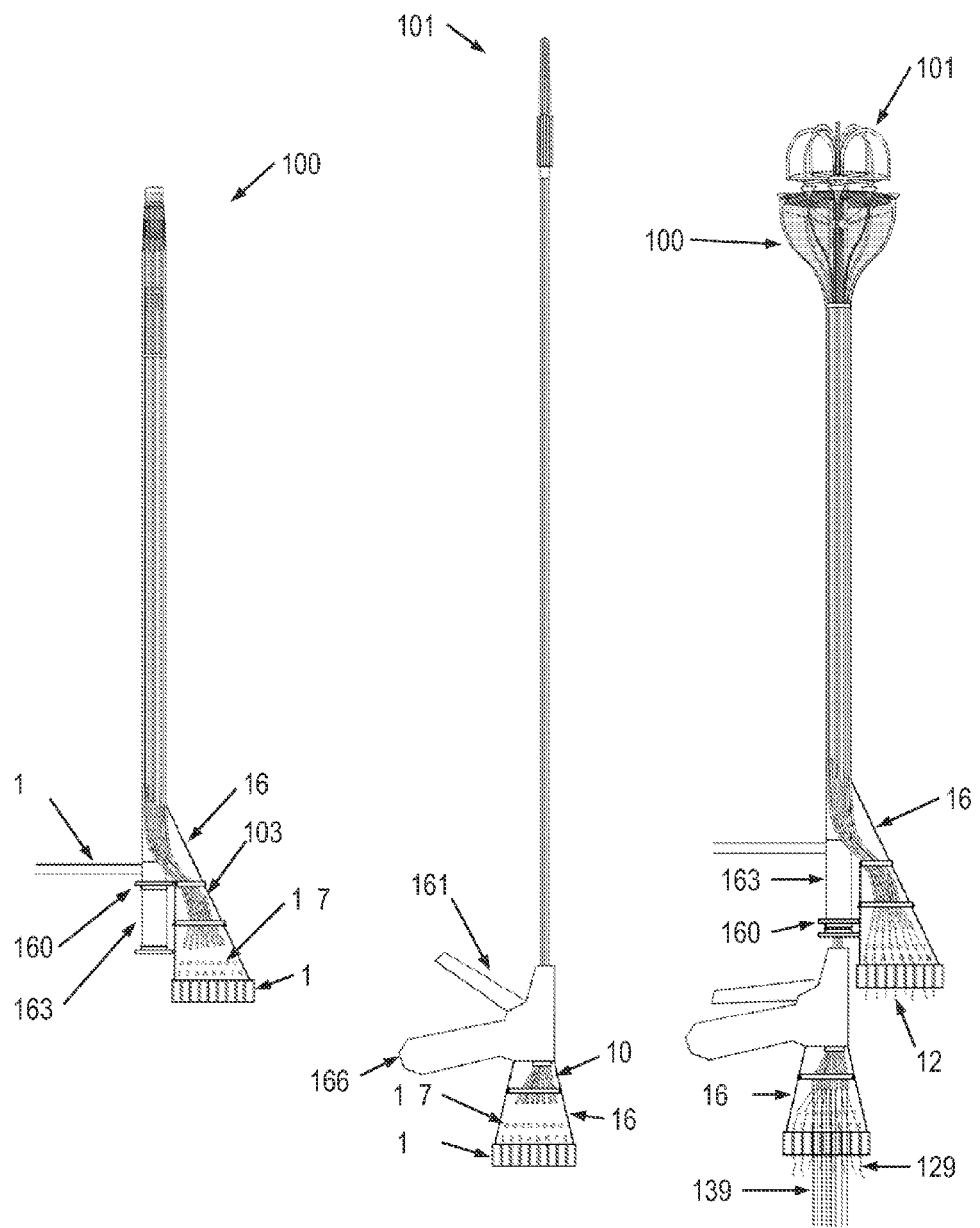
FIG. 21A is a schematic diagram illustrating a view of an un-expanded outer tube component.
FIG. 21B is a schematic diagram illustrating a view of an un-expanded suture delivery tube set component.
FIG. 21C is a schematic diagram illustrating a view of an expanded outer tube component incorporated with an expanded suture delivery tube set component.

FIGS. 21A, 21B, and 21C illustrate views demonstrating the full length of the un-expanded outer tube component 100, the full length of the suture delivery tube set component 101, and the full length of the expanded outer tube component 100 incorporated with, and coupled to, the expanded suture delivery tube set component 101.

Optionally, the length of the outer tube component 100 may optionally range from 25 to 50 inches. The outer tube component's 100 unexpanded outer diameter may optionally range from 13 mm to 22 mm. The outer tube component's 100 expanded distal end's outer diameter may optionally range from 25 mm to 100 mm. The length of the suture delivery tube set component 101 may optionally range from 31 to 56 inches. The outer diameter of the suture delivery tube set component 101 may optionally range from 5 mm to 15 mm.

FIG. 21A illustrates the attachment of the vacuum tube 158 to the distal end of the central tube 106 of the outer tube component 100. FIG. 20A also illustrates the expansion actuation mechanism 160, which by sliding the ring-shaped trigger proximally up the contained tube handle 163 elevates the activation wires 116 within their containing tubes 155, thereby elevating the distal holey tube segment 107, thereby activating the umbrella-like expansion of the distal end of the outer tube component 100 as described earlier. FIG. 21A also illustrates the outer tube component's proximal end control mount 164 which maintains the proximal ends of the receiving tubes 103, funnel maintaining thread retaining pegs 147, and thread/suture holding component 148. The funnel maintaining thread retaining pegs 147 serve by having the funnel maintaining threads 125 wrapped around the peg 147 and then the threads are held by the thread/suture holding component 148.

FIG. 21B illustrates the reconfiguration activation handle 166 and trigger 161 of the suture delivery tube set component's 101 proximal end, which by compressing the trigger 161 toward the reconfiguration activation handle 166 elevates the series of warping cables 122 contained within the central warping cable tube 123, thereby shortening the length of the exposed individual warping cables 122 incorporated with the delivery tube circumferential support platform 121 and attached to the distal ends of the delivery tubes 104, thereby bending the distal ends of the delivery tubes 104 into their suture deployment configuration.

FIG. 21C illustrates the suture delivery tube set component 101 inserted into the outer tube component 100 and further illustrating the expanded and coupled distal ends of the two components 100, 101. The activation handle 163 of the outer tube component 100 and the activation handle 166 of the suture delivery tube set component 101 are in their engaged configuration. The distal end of the suture delivery tube set component 101 is expanded containing the distal ends of the suture needles 139 of the device with their proximal ends 139 extending out of the proximal ends of the delivery tubes 104.

Figure 22A:
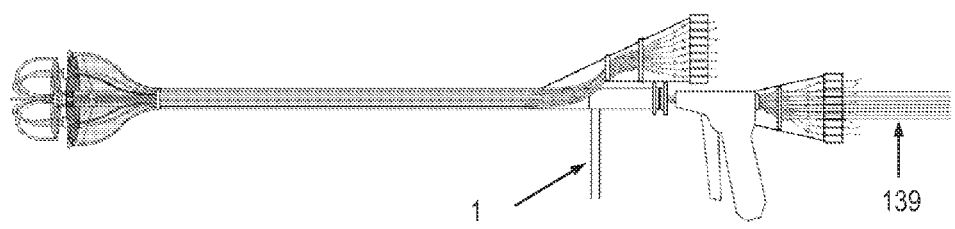
FIG. 22A is a schematic diagram illustrating a view of the device with needles loaded for deployment.
Figure 22B:
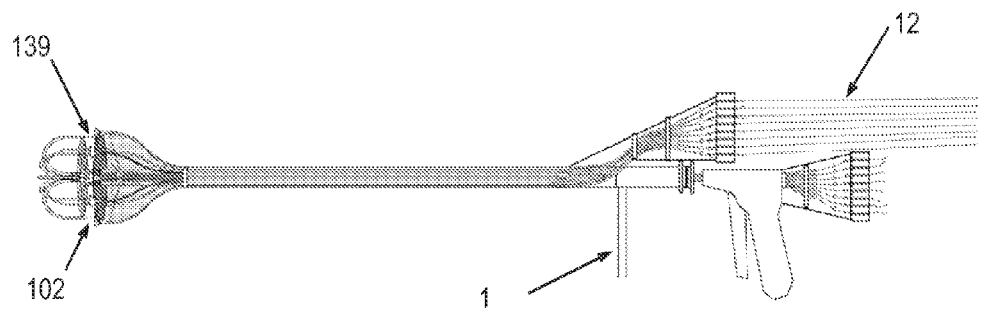
FIG. 22B is a schematic diagram illustrating a view of the device with needles deployed.

FIGS. 22A and 22B illustrate the passage of suture needles from the suture delivery tube set component's 101 delivery tubes 104, across the suction gap 102 also referred to herein as circumferential gap, and into and through the receiving tubes 103 of the outer tube component 100. FIG. 22A illustrates the suture delivery tube set component 101 loaded with needles 139 attached to sutures 128 which are attached to suture anchors 140. The needles 139 are manually or mechanically advanced through the delivery tubes 104 by pushing. The needles 139 traverse the suction gap 102 and subsequently enter the distal ends of the receiving tubes 103. The needles 139 continue to advance up the receiving tubes 103 until their distal tips emerge out of the proximal end of the receiving tubes 103. Subsequently the operator may grasp the distal end of the needle 139 and pull the entire length of the needle through and out of the receiving tube 103 with the attached suture 128 trailing behind. The suture 128 is pulled until the suture anchor 140 or attached graft prevents its further advancement due to its incorporation with tissue. The components of the device are subsequently un-expanded and withdrawn from the patient and the proximal graft 127 is incorporated with the sutures 128 and secured to the distal graft 142.

Figure 23:
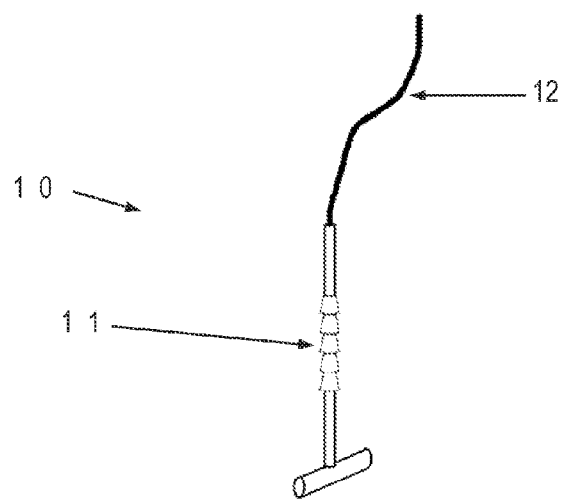
FIG. 23 is a schematic diagram illustrating a view of a suture anchor with a ribbed shaft.

FIG. 23 illustrates a suture anchor 140 attached to a suture 128. Optionally, the vertical length of the suture anchor 140 has a ribbed shaft such that each protrusion 151 of the ribbed shaft is configured to have a larger diameter at its distal end than the diameter of the protrusion 151 at its proximal end. This configuration enables the ribbed shaft to pass through an aperture of a size in a forward direction, but not allow the ribbed shaft to pass through the aperture of a size in a reverse direction. Use of a suture anchor 140 with a ribbed shaft enables a proximal graft 142 to be fixed to the suture anchor by advancing the ribbed shaft through an aperture of a size in the body of the proximal graft 142. Optionally, the ribbed shafts may pass freely through the body of the proximal graft and then have fitted caps slid into place and fixed onto the ribbed shafts, thereby entrapping the proximal graft beneath the fitted caps.

Figure 24:
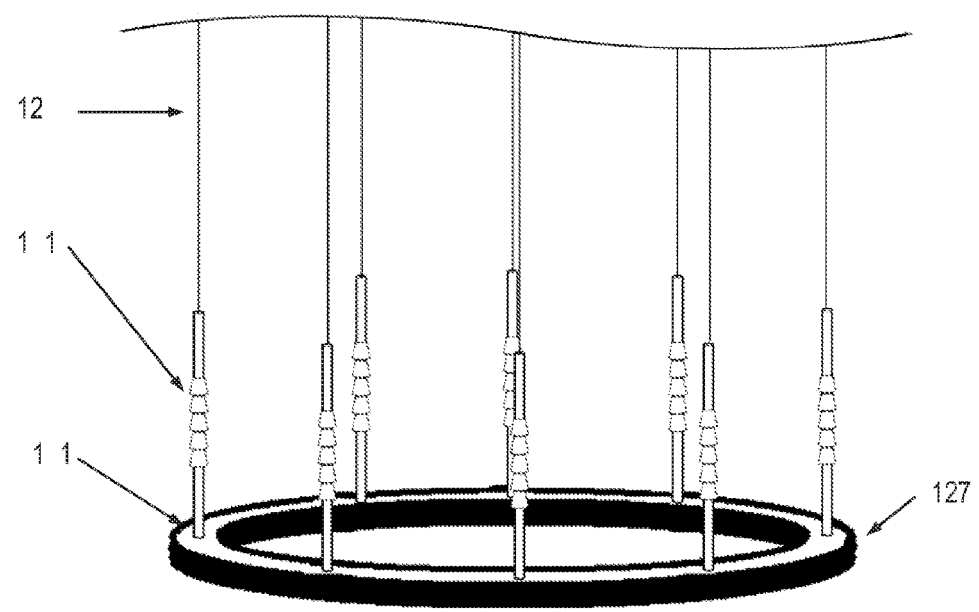
FIG. 24 is a schematic diagram illustrating a view of a ring graft incorporated with ribbed shafts.

FIG. 24 illustrates a distal ring graft 127 with a series of ribbed shafts 151 positioned around the circumference of the ring graft 127 with a direct attachment 141 to its body. Optionally, the distal ring graft 127 is able to be fixed to a proximal ring graft 142 by means of advancing the ribbed shafts 151 of the connected distal ring 127, through apertures in the body of the proximal ring graft 142.

FIGS. 25A-25L illustrates the implantation of a distal ring graft and a proximal ring graft, fixed together with connecting sutures, and with a circumferential plication of tissue incorporated and secured between the two rings. As described above, the circumferential gap can allow 2.0 cm or more serosal-to-serosal tissue to be drawn radially into the gap, which can form a circumferential invagination or plication of tissue to be sutured. For example, the serosal-to-serosal tissue invaginated into the gap, creating a plication, can be drawn in circumferentially around the gap. Optionally, tissue is drawn in such that the distance from the medial extent of tissue invagination, or plication, to one or more suture delivery tube opening or one or more suture receiving opening is about 3.0 cm or more.

Figure 25A:
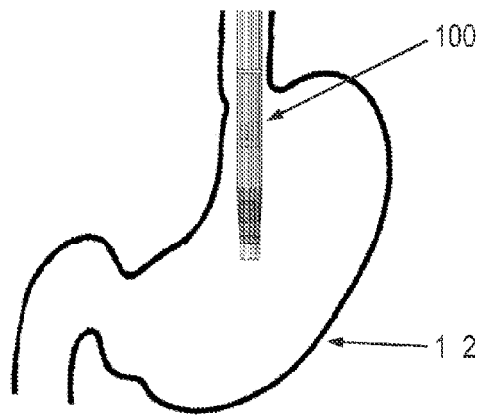
FIG. 25A is a schematic diagram illustrating a view of an unexpanded outer tube in a stomach.

FIG. 25A illustrates the un-expanded distal end of the outer tube component 100 inserted into a stomach 152. Subsequent to insertion of the un-expanded outer tube component 100 into the stomach 152, which must first pass through the patient's mouth and esophagus, the stiffening wires 112 are inserted into the expansion rib tubes 111.

Figure 25B:
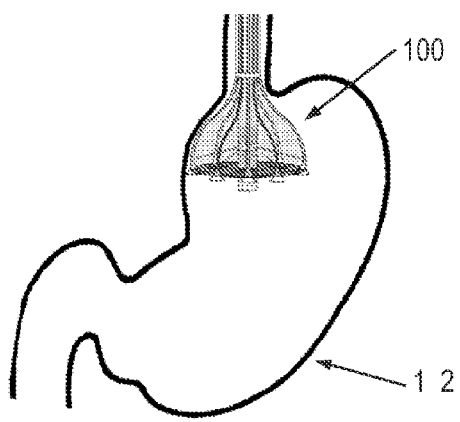
FIG. 25B is a schematic diagram illustrating a view of an expanded outer tube in a stomach.

FIG. 25B illustrates the expanded outer tube component 100 with the funnel tips 105 deployed and held in the distal ends of the receiving tubes 103. The outer tube component 100 is pulled proximally by the operator until the expanded distal end of the outer tube component 100 is positioned in the proximal stomach, distal to the gastroesophageal junction. An endoscope may be inserted through the outer tube component's central tube 106 and retroflexed to visually inspect the stomach, the secure deployment of the funnels 105, and the position of the component 100 within the stomach.

Figure 25C:
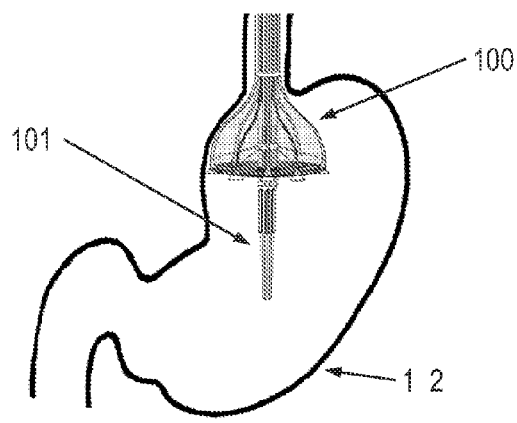
FIG. 25C is a schematic diagram illustrating a view of an expanded outer tube incorporated with an un-expanded suture delivery tube set in a stomach.

FIG. 25C illustrates the suture delivery tube set component's 101 insertion through the distal end central tube 106 of the expanded outer tube component 100. The distal end of the suture delivery tube set component 101 is properly positioned for the reconfiguration the delivery tubes 104.

Figure 25D:
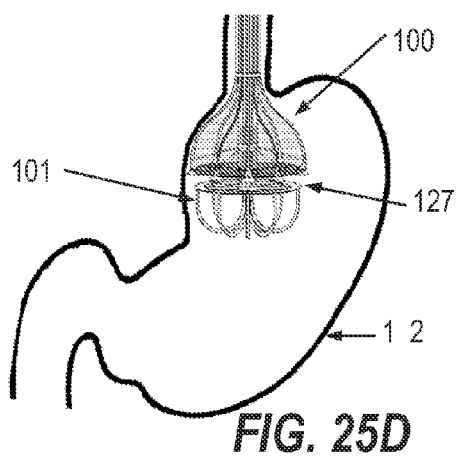
FIG. 25D is a schematic diagram illustrating a view of an expanded outer tube incorporated with an expanded suture delivery tube set in a stomach.
Figure 25E:
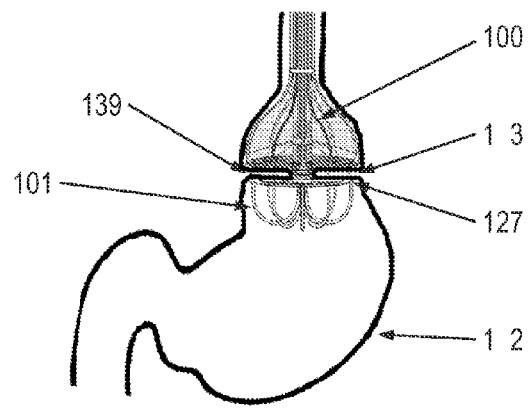
FIG. 25E is a schematic diagram illustrating a view of an expanded outer tube incorporated with an expanded suture delivery tube set with distal ring graft and sutures incorporated with tissue in a stomach.
Figure 25F:
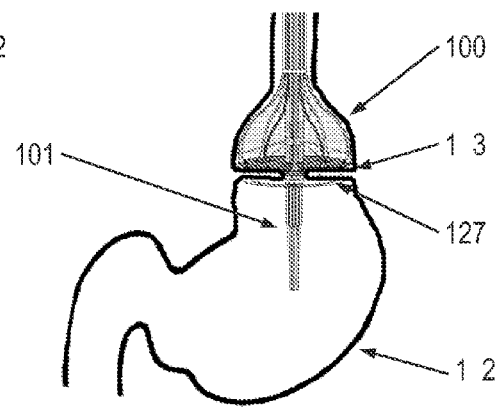
FIG. 25F is a schematic diagram illustrating a view of an expanded outer tube incorporated with an un-expanded suture delivery tube set with distal ring graft and sutures incorporated with tissue in a stomach.

FIG. 25D illustrates the expanded suture delivery tube set component 101 coupled to the expanded outer tube component 100 and with the distal ring graft 127 advanced and pulled into position by the directly attached sutures 128, or, optionally, by the ring graft maintenance threads 129. The assembled device is properly configured and positioned for suture deployment.

FIG. 25E illustrates the properly configured and positioned assembled device with a vacuum applied to the outer tube component 100, such that the full-thickness of the circumference of the stomach's wall 153 is drawn into the suction gap 102 of the device. The needles 139 are subsequently advanced from the distal end of the delivery tubes 104 across the suction gap 102, and into the receiving tubes 103, thereby traversing the drawn in tissue 153. The needles 139 are advanced completely through the receiving tubes 103 and the attached sutures 127 are drawn taught.

FIG. 25F illustrates the reconfiguration of the distal end of the suture delivery tube set component 101 into its linear configuration. The delivery tubes 104 of the suture delivery tube set component are empty.

Figure 25G:
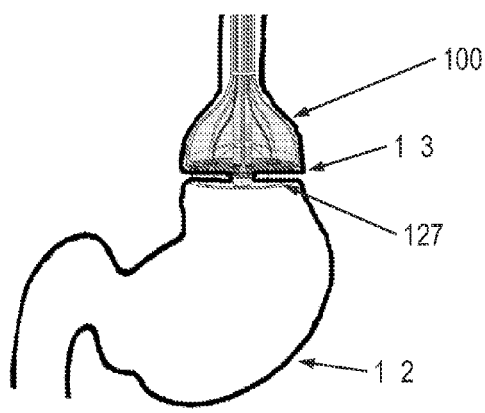
FIG. 25G is a schematic diagram illustrating a view of an expanded outer tube with distal ring graft and sutures incorporated with tissue in a stomach

FIG. 25G illustrates the suture delivery tube set component 101 having been withdrawn from the central tube 106 of outer tube component 100. The distal ring graft 127 is left behind, held in place by the sutures 128 distal to the incorporated tissue 153.

Figure 25H:
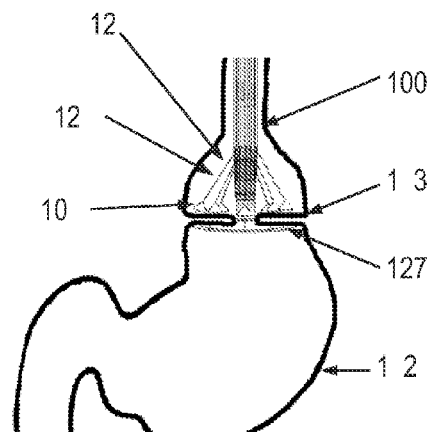
FIG. 25H is a schematic diagram illustrating a view of an unexpanded outer tube with a distal ring graft and sutures incorporated with tissue in a stomach.

FIG. 25H illustrates the un-expanded outer tube component 100 as it is withdrawn from the stomach 152. The funnels 105 remain in place proximal to the incorporated tissue 153 and encircling the individual sutures 128 which have been passed through them.

Figure 25I:
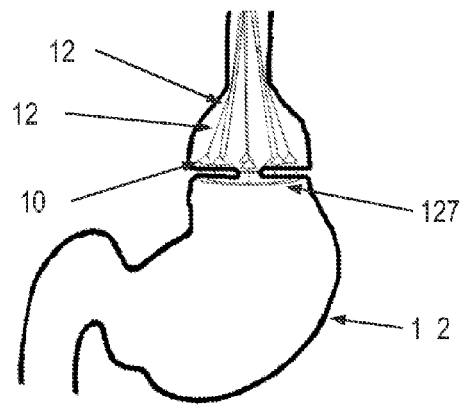
FIG. 25I is a schematic diagram illustrating a view of a funnel tips and distal ring graft and sutures incorporated with tissue in a stomach.

FIG. 25I illustrates the stomach 152 with the outer tube component withdrawn from the stomach, the distal ring 127 in place, the circumferential plication of tissue 153 incorporated with sutures 128, and the funnels 105 with their attached funnel threads 125 in place encircling the individual sutures 128 which have been passed through them.

Figure 25J:
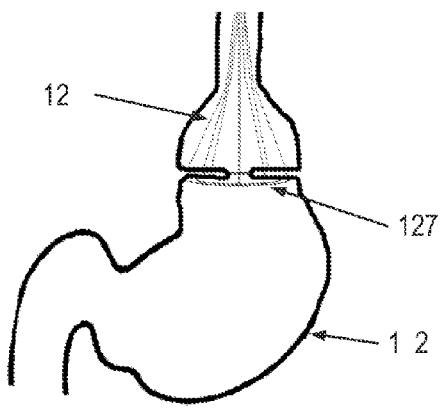
FIG. 25J is a schematic diagram illustrating a view of a distal ring graft and sutures incorporated with tissue in a stomach.

FIG. 25J illustrates the stomach 152, the distal ring graft 127, and the circumferential plication of tissue 153 incorporated with sutures, wherein the funnels 105 have been withdrawn from the stomach 152 by pulling the funnel threads 125 up and off of the distal end of the suture needles 139.

Figure 25K:
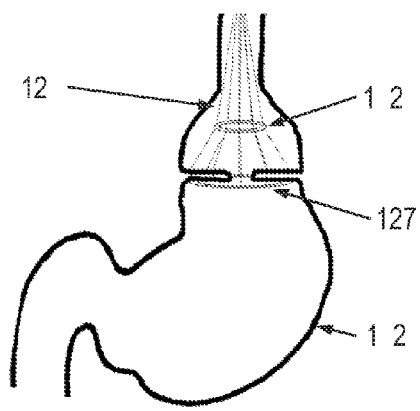
FIG. 25K is a schematic diagram illustrating a view of a distal ring graft and sutures and a proximal ring graft incorporated with tissue in a stomach.

FIG. 25K illustrates a proximal ring graft 142 which has been incorporated with the series of sutures 128 and has been parachuted into position proximal to the circumferential plication of tissue 153 and the distal ring graft 127.

Figure 25L:
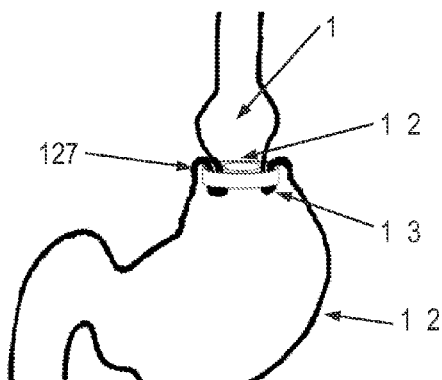
FIG. 25L is a schematic diagram illustrating a view of a distal ring graft and sutures and a proximal ring graft incorporated with tissue and secured in a stomach.

FIG. 25L illustrates the completed implantation of a distal ring graft 127 and a proximal ring graft 142, fixed together with connecting sutures 128, and with a circumferential plication of tissue 153 incorporated and secured between the two rings in the proximal stomach. Subsequent to parachuting the proximal ring graft 142 into position, a ring pusher or endoscope is used to advance the proximal ring 142 into position adjacent to the incorporated tissue 153 with tension being maintained on the distal end of the sutures 128, thereby securing the proximal ring 142 to the distal ring 127 as described earlier. The lengths of suture 128 proximal to their incorporation with the proximal ring 142 are cut using endoscopic instrumentation. The result of the procedure is a constriction in the proximal stomach utilized to impede the flow of ingested food, thereby decreasing food intake.

The disclosed devices, systems and methods optionally reduce the invasiveness of suturing within hollow organ or body cavity and/or reduce the complications from abdominal surgical procedures such as gastric bypass surgery. The disclosed devices, systems and methods optionally minimize or eliminate the incisions required to perform gastric banding and gastric bypass surgery. The multi-component design allows for a small diameter delivery device that can be more easily inserted into the stomach through the esophagus. Moreover, the multi-component design, alone or in addition to the removable support rods, also provide increased safety and comfort by increasing flexibility of the device during insertion into the stomach.

A number of embodiments of the invention have been described. Nevertheless, it will be understood that various modifications may be made without departing from the spirit and scope of the invention. Accordingly, other embodiments are within the scope of the following claims. As used throughout, the term exemplary means example. Thus, for example, and exemplary dimension is and example, or optional dimension and other examples or optional dimensions can also be used.

Disclosed are materials, systems, devices, compositions, and components that can be used for, can be used in conjunction with, can be used in preparation for, or are products of the disclosed methods, systems and devices. These and other components are disclosed herein, and it is understood that when combinations, subsets, interactions, groups, etc. of these components are disclosed that while specific reference of each various individual and collective combinations and permutations of these components may not be explicitly disclosed, each is specifically contemplated and described herein. For example, if a method is disclosed and discussed each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed systems or devices. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the materials for which they are cited are hereby specifically incorporated by reference in their entireties.

What is claimed is:

1. A system for deploying sutures within a hollow organ, comprising:
   a. a central tube having a lumen and an open distal end;
   b. an expandable enclosure located to surround the central tube, wherein the expandable enclosure is defined by a distal air-permeable surface and a lateral non air-permeable surface,
   wherein the expandable enclosure is movable between a retracted configuration and an expanded configuration; and
   c. an expandable suture delivery apparatus having a plurality of suture delivery tubes, each suture delivery tube having an open distal end, the apparatus being configured for movement between a retracted configuration and an expanded configuration,
   wherein the suture delivery apparatus is slideably moveable through the central tube lumen while the suture delivery apparatus is in the retracted configuration and wherein the open distal end of one or more of the suture delivery tubes are distally spaced from the expandable enclosure while the suture delivery apparatus is in the expanded configuration.

2. The system of claim 1, wherein the open distal ends of the suture delivery tubes are spaced from each other and are arranged circumferentially about the suture delivery apparatus when the suture delivery apparatus is in the expanded configuration.

3. The system of claim 2, wherein the distal spacing between the suture delivery apparatus and the expandable enclosure define a circumferential gap between the suture delivery apparatus and the expandable enclosure that is configured to receive tissue of the organ.

4. The system of claim 3, wherein the suture delivery apparatus comprises an air-impermeable surface that defines a distal portion of the circumferential gap.

5. The system of claim 3, wherein the central tube comprises a suction port in communication with the lumen of the central tube, the suction port adapted to be placed in communication with a suction source to evacuate air from the central tube lumen.

6. The system of claim 5, wherein the evacuation of air from the central tube lumen by the suction source causes organ tissue to enter the circumferential gap.

7. The system of claim 1, further comprising an actuator mechanism configured for moving the enclosure between its retracted and expanded configuration.

8. The system of claim 7, further comprising an actuator mechanism configured for moving the suture delivery apparatus between its retracted and expanded configuration.

9. The system of claim 8, wherein the actuator mechanism is configured for remote operation by an operator located outside of the organ lumen.

10. The system of claim 1, further comprising a distal ring graft positionable proximal to the open distal ends of the suture delivery tubes.

11. The system of claim 10, wherein the distal ring graft is moveable through the central tube lumen.

12. The system of claim 10, further comprising a proximal ring graft positionable proximal to the distal ring graft.

13. The system of claim 1, wherein the open distal end of the central tube is positionable in the lumen of the hollow organ.

14. The system of claim 13, wherein the enclosure and suture delivery apparatus are moveable between their expanded and retracted configurations within the organ lumen.

15. The system of claim 13, wherein the enclosure and suture delivery apparatus are introduced into the organ lumen or removed from the organ lumen in their retracted configurations.

16. The system of claim 1, further comprising:
   a. a plurality of flexible support tubes positioned about the central tube; and
   b. a plurality of multi-segmented support rods, wherein the support tubes are configured to accept the multi-segmented support rods.

17. The system of claim 1, wherein the expandable enclosure includes a plurality of expansion rib tubes positioned to encircle the central tube.

18. The system of claim 17, further comprising:
   a plurality of stiffening wires, wherein the plurality of expansion rib tubes are configured to receive the plurality of stiffening wires,
   wherein the plurality of stiffening wires and the plurality of expansion rib tubes are configured to vertically support the expandable enclosure when the enclosure is in the expanded configuration and the plurality of stiffening wires are inserted into the plurality of expansion rib tubes.

19. The system of claim 1, wherein:
   the expandable enclosure includes a plurality of suture receiving tubes, each suture receiving tube having an open distal end.

20. A system for deploying sutures within a hollow organ, comprising:
   a. a central tube having an outer surface and a lumen with an open distal end;
   b. a proximal enclosure surrounding the central tube,
   wherein the enclosure is moveable between a retracted configuration and an expanded configuration; and
   c. a distal suture delivery apparatus having a plurality of suture delivery tubes, each suture delivery tube having an open distal end,
   wherein the suture delivery apparatus is moveable between a retracted configuration and an expanded configuration,
   wherein in the expanded configuration, the expanded enclosure is spaced from the expanded suture delivery apparatus to define a circumferential gap therebetween the enclosure and the suture delivery apparatus,
   wherein the circumferential gap is defined by a portion of the outer surface of the central tube,
   wherein the proximal enclosure includes a plurality of suture receiving tubes, each suture receiving tube having an open distal end, and wherein the suture delivery apparatus is slideably moveable through the central tube lumen while the suture delivery apparatus is in the retracted configuration.

21. The system of claim 20, wherein:
the proximal enclosure includes a distal air-permeable surface; and
the air-permeable surface defines a distal portion of the circumferential gap.

22. The system of claim 20, wherein the enclosure includes a plurality of expansion rib tubes positioned to encircle the central tube, and the system further comprises:
   a plurality of stiffening wires, wherein the plurality of expansion rib tubes are configured to receive the plurality of stiffening wires,
   wherein the plurality of stiffening wires and the plurality of expansion rib tubes are configured to vertically support the enclosure when the enclosure is in the expanded configuration and the plurality of stiffening wires are inserted into the plurality of expansion rib tubes.

23. A system for deploying sutures within a hollow organ, comprising:
   a. a central tube having an outer surface and a lumen with an open distal end;
   b. a proximal enclosure surrounding the central tube, wherein the enclosure is moveable between a retracted configuration and an expanded configuration; and
   c. a distal suture delivery apparatus having a plurality of suture delivery tubes, each suture delivery tube having an open distal end,
   wherein the suture delivery apparatus is moveable between a retracted configuration and an expanded configuration, and
   wherein the suture delivery apparatus is slideably moveable through the central tube lumen while the suture delivery apparatus is in the retracted configuration.

24. The system of claim 23, wherein:
in the expanded configuration, the expanded enclosure is spaced from the expanded suture delivery apparatus to define a circumferential gap therebetween the enclosure and the delivery apparatus, and
the circumferential gap is defined by a portion of the outer surface of the central tube.

25. The system of claim 24, wherein:
the proximal enclosure includes a distal air-permeable surface; and
the air-permeable surface defines a distal portion of the circumferential gap.

26. The system of claim 23, wherein the enclosure includes a plurality of expansion rib tubes positioned to encircle the central tube, and the system further comprises:
   a plurality of stiffening wires, wherein the plurality of expansion rib tubes are configured to receive the plurality of stiffening wires,
   wherein the plurality of stiffening wires and the plurality of expansion rib tubes are configured to vertically support the enclosure when the enclosure is in the expanded configuration and the plurality of stiffening wires are inserted into the plurality of expansion rib tubes.

* * * * *